US005547867A

United States Patent [19]

Kara et al.

[11] Patent Number: 5,547,867

[45] Date of Patent: Aug. 20, 1996

[54] FERMENTATION PROCESSES FOR PREPARING SOLUBLE RICIN A

[75] Inventors: Bhuphendra V. Kara, Runcorn; Robert C. Hockney, Macclesfield; John E. Fitton, Buxton, all of England

[73] Assignee: Imperial Chemical Industries PLC, London, England

[21] Appl. No.: 218,303

[22] Filed: Mar. 28, 1994

Related U.S. Application Data

[63] Continuation of Ser. No. 841,533, Feb. 26, 1992, abandoned.

[30] Foreign Application Priority Data

| | | | |
|---|---|---|---|
| Feb. 26, 1991 | [DE] | Germany | 9104016 |
| Feb. 26, 1991 | [GB] | United Kingdom | 9103925 |
| Feb. 26, 1991 | [GB] | United Kingdom | 9103926 |

[51] Int. Cl.[6] .......... C12N 9/22; C12N 15/29; C12P 21/02; C07K 14/415

[52] U.S. Cl. .......... 435/199; 435/691; 530/412

[58] Field of Search .......... 435/199, 69.1; 530/412

[56] References Cited

U.S. PATENT DOCUMENTS

| | | | |
|---|---|---|---|
| 4,689,401 | 8/1987 | Ferris | 530/396 |
| 4,894,334 | 1/1990 | Ben-Bassat et al. | 435/69.1 |

FOREIGN PATENT DOCUMENTS

| | | |
|---|---|---|
| 144064 | 6/1985 | European Pat. Off. . |
| 152483 | 8/1985 | European Pat. Off. . |
| 237676 | 8/1987 | European Pat. Off. . |
| 279665 | 8/1988 | European Pat. Off. . |
| 9113156 | 9/1991 | WIPO . |

OTHER PUBLICATIONS

L. B. Tsai 'The Effect Of Organic Nitrogen And Glucose On The Production Of Recombinant Human Insulin–Like Growth Factor In High Cell Density *Escherichia Coli* Fermentations' Journal Of Indus Microbiology, Aug. 1987, pp. 181–186.

LI, 'The Production Of Recombinant Beta–Galactosidase In *Escherichia Coli* In Yeast Extract Enriched Medium' Journal For Industrial Microbiology, 1990 pp. 85–93.

O'Hare, et al (1987) Febs Letters 216 73–78.

Wilkinson et al (1991) Biotechnology 9 443–448.

Schein (1989) Biotechnology 7 1141–1149.

Piatak et al (1988) J. Biological Chemistry 263 4837–4843.

Kopetzki et al (1989) Mol. Gen. Gevet. 216 149–155.

*Primary Examiner*—Robert A. Wax
*Assistant Examiner*—G. E. Bugalsky
*Attorney, Agent, or Firm*—Cushman Darby & Cushman, L.L.P.

[57] ABSTRACT

Processes for preparing polypeptides such as ricin A such that soluble polypeptide may be obtained. The pH may be adjusted during the process or the temperature decreased during the terminal portion of the cultivation, and yeast extract may be added to the growth medium during the cultivation. In the case of ricin A the pH is generally adjusted by lowering the pH from a first value such as 6.7 to a second value such as a value between about 5.5 and 6.7.

13 Claims, 27 Drawing Sheets

CONSTRUCTION OF pICI0020

Fig. 9A

```
                     Trp Promoter
     TTCTGGCAAATATTCTGAAATGAGCTGTTGACAATTAATCATCGAACTAGTTAACTAGTA
   1 ---------+---------+---------+---------+---------+---------+  60

                     S-D   rbs   Met KpnI     BamHI
     CGCAAGTTCACGTAAAAAGGGTATCGACAATGGTACCCGGGGATCCACCTCAGGGTGGTC
  61 ---------+---------+---------+---------+---------+---------+ 120

             Stop            KpnI        ----Ricin A----->
     TTTCACATTAGAGGATAACAACATGGTACCCAAACAATACCCAATTATAAACTTTACCAC
 121 ---------+---------+---------+---------+---------+---------+ 180
                             M  V  P  K  Q  Y  P  I  I  N  F  T  T

     AGCGGGTGCCACTGTGCAAAGCTACACAAACTTTATCAGAGCTGTTCGCGGTCGTTTAAC
 181 ---------+---------+---------+---------+---------+---------+ 240
      A  G  A  T  V  Q  S  Y  T  N  F  I  R  A  V  R  G  R  L  T

     AACTGGAGCTGATGTGAGACATGAAATACCAGTGTTGCCAAACAGAGTTGGTTTGCCTAT
 241 ---------+---------+---------+---------+---------+---------+ 300
      T  G  A  D  V  R  H  E  I  P  V  L  P  N  R  V  G  L  P  I
```

Fig. 9B

```
    AAACCAACGGTTTATTTTAGTTGAACTCTCAAATCATGCAGAGCTTTCTGTTACATTAGC
301 ---------+---------+---------+---------+---------+---------+ 360
     N  Q  R  F  I  L  V  E  L  S  N  H  A  E  L  S  V  T  L  A

    CCTGGATGTCACCAATGCATATGTGGTCGGCTACCGTGCTGGAAATAGCGCATATTTCTT
361 ---------+---------+---------+---------+---------+---------+ 420
     L  D  V  T  N  A  Y  V  V  G  Y  R  A  G  N  S  A  Y  F  F

    TCATCCTGACAATCAGGAAGATGCAGAAGCAATCACTCATCTTTTCACTGATGTTCAAAA
421 ---------+---------+---------+---------+---------+---------+ 480
     H  P  D  N  Q  E  D  A  E  A  I  T  H  L  F  T  D  V  Q  N

    TCGATATACATTCGCCTTTGGTGGTAATTATGATAGACTTGAACAACTTGCTGGTAATCT
481 ---------+---------+---------+---------+---------+---------+ 540
     R  Y  T  F  A  F  G  G  N  Y  D  R  L  E  Q  L  A  G  N  L

    GAGAGAAAATATCGAGTTGGGAAATGGTCCACTAGAGGAGGCTATCTCAGCGCTTTATTA
541 ---------+---------+---------+---------+---------+---------+ 600
     R  E  N  I  E  L  G  N  G  P  L  E  E  A  I  S  A  L  Y  Y
```

Fig. 9C

```
     TTACAGTACTGGTGGCACTCAGCTTCCAACTCTGGCTCGTTCCTTTATAATTTGCATCCA
601  ---------+---------+---------+---------+---------+---------+ 660
      Y  S  T  G  G  T  Q  L  P  T  L  A  R  S  F  I  I  C  I  Q

     AATGATTTCAGAAGCAGCAAGATTCCAATATATTGAGGGAGAAATGCGCACGAGAATTAG
661  ---------+---------+---------+---------+---------+---------+ 720
      M  I  S  E  A  A  R  F  Q  Y  I  E  G  E  M  R  T  R  I  R

     GTACAACCGGAGATCTGCACCAGATCCTAGCGTAATTACACTTGAGAATAGTTGGGGGAG
721  ---------+---------+---------+---------+---------+---------+ 780
      Y  N  R  R  S  A  P  D  P  S  V  I  T  L  E  N  S  W  G  R

     ACTTTCCACTGCAATTCAAGAGTCTAACCAAGGAGCCTTTGCTAGTCCAATTCAACTGCA
781  ---------+---------+---------+---------+---------+---------+ 840
      L  S  T  A  I  Q  E  S  N  Q  G  A  F  A  S  P  I  Q  L  Q
```

Fig. 9D

```
     AAGACGTAATGGTTCCAAATTCAGTGTGTACGATGTGAGTATATTAATCCCTATCATAGC
 841 ---------+---------+---------+---------+---------+---------+ 900
      R  R  N  G  S  K  F  S  V  Y  D  V  S  I  L  I  P  I  I  A

     TCTCATGGTGTATAGATGCGCACCTCCACCATCGTCACAGTTTTGATTGCTTATAAGGCC
 901 ---------+---------+---------+---------+---------+---------+ 960
      L  M  V  Y  R  C  A  P  P  P  S  S  Q  F  *

        KpnI           XbaI        PstI  SphI HindIII
     AGTGGTACCCGGGGATCCTCTAGAGTCGACCTGCAGGCATGCAAGCTTAGCCCGCCTAAT
 961 ---------+---------+---------+---------+---------+---------+1020

        Terminator
     GAGCGGGCTTTTTTTTATCGACCGATGCCCTTGAGAGCCTTCAACCCAGTCAGCTCCTTC
1021 ---------+---------+---------+---------+---------+---------+1080

     CGGTGGGCGCGGGGCATGACTATCGTCGCCGCACTTATGACTGTCTTCTTTATCATGCAA
1081 ---------+---------+---------+---------+---------+---------+1140
```

CONSTRUCTION OF pICI1102

Fig. 11.

EcoRI

AATTCTGGCA AATATTCTGA AATGAGCTGT TGACAATTAA TCATCGAACT

AGTTAACTAG TACGCAAGTT CACGTAAAAA GGGTATCGAC

KpnI BamHI XbaI SalI PstI SphI

AATGGTACCC GGGGATCCTC TAGAGTCGAC CTGCAGGCAT GCAAGCTTAG

ClaI/AccI

CCCGCCTAAT GAGCGGGCTT TTTTTTATCG AC

Fig. 13.

SalI

5′ TCGACATTATATTACTAATTAATTGGGGACCCTAGAGGTCCCCTTTTTTATTTTAA

3′ GTAATATAATGATTAATTAACCCCTGGGATCTCCAGGGGAAAAAATAAAATT

SphI BamHI StyI

AAAGCATGCGGATCCC 3′

TTTCGTACGCCTAGGGGAAC 5′

FERMENTATION PROCESSES FOR PREPARING SOLUBLE RICIN A

This is a continuation of application Ser. No. 07/841,533, filed on Feb. 26, 1992, now abandoned.

This invention relates to the field of biotechnology and is particularly concerned with processes for preparing soluble recombinant molecules.

Generally when recombinant proteins are prepared in bacterial hosts, such as *E. coli*, the fermentation is carried out under conditions which favour growth, that is at a temperature of about 37° C. and a pH of about 6.8.

The fermentation process is usually carried out in a medium which contains those nutrients which fulfill the cellular growth requirements of the host. Typically the growth medium includes sources of carbon and nitrogen for synthesis of cellular components and energy, ions such as sulphate, phosphate, magnesium, calcium, iron and various trace elements. Yeast extract is also often present as a component of the growth medium. For example, Luria Broth contains about 0.5% yeast extract in addition to tryptone and sodium chloride. Recently it has been reported (X Li, J W Robbins and K B Taylor: Journal of Industrial Microbiology, 5, 85–94, 1990) that when Luria Broth is enriched with yeast extract so that it contains 1 to 3% yeast extract biomass and β-galactosidase expression is increased. It has also been reported (L. B. Tsai et al, Journal of Industrial Microbiology, 2, 181–187, 1987) that recombinant human insulin-like growth factor can be prepared as inclusion bodies by feeding of yeast extract and glucose into the fermentation broth in a fed-batch process.

U.S. Pat. No. 4,894,334 describes a process for the preparation of ricin A in which the cultivation is carried out at 37° C. and at a pH of 6.8, and a 2% solution of casamino acid is added when the turbidity of the growth medium is about $OD_{680}$ of 10.

When many polypeptides are prepared by recombinant DNA technology in *E. coli* the polypeptide is obtained in an insoluble form, for example as insoluble aggregates or inclusion bodies. If this material is to be used, it has to be made soluble to permit renaturation into biologically active form. This solubilisation step generally requires the use of chemicals, such as detergents or chaotropic agents, which are tedious and expensive to use and can lead to chemical modification of the protein.

The production of insoluble material tends to occur when recombinant ricin A is prepared. For example, it is reported in EP 237,676 that expression of ricin A in *E. coli* at 37° C., pH 6.8 leads to insoluble material which has to be solubilised by treatment with a mixture of urea and SDS. EP 237,676 reports that soluble ricin A is produced when the coding sequence for ricin A is placed in direct reading frame with the DNA encoding the leader sequence of the alkaline phosphatase structural gene (phoA) of *E. coli* K12.

Ricin and ricin-type molecules, such as abrin, are known compounds which are produced by plant cells, and which possess cytotoxic properties. Toxins of this type consist of two polypeptide chains which are linked via a disulphide bridge. One of the polypeptide chains (the "A chain") is primarily responsible for the cytotoxic properties of the toxin molecule; whilst the other polypeptide chain (the "B chain") enables the toxin molecule to bind to cell surfaces.

The toxicity of ricin is dependent upon three distinguishable events:

(i) binding of the ricin molecule to the cell surface through interaction of galactose binding sites on the B chain with glycoproteins or glycolipids exposed at the cell surface;

(ii) penetration of at least the A chain into the cytosol of the cell; and (iii) enzymic cleavage of RNA in the 60S sub-unit of the ribosome leading to inhibition of protein synthesis and ultimately cell death.

It is also believed that the B chain plays an important secondary function, apart from its primary function of binding the ricin molecule to the cell surface, in that it facilitates uptake of ricin into the cell. Thus separated A and B chains are essentially non-toxic since the B chain is not cytotoxic, and the A chain lacks the ability to bind to cell surfaces and penetrate into the cytosol of the cell in the absence of the B chain.

It has already been suggested that the toxicity of the A chain of ricin might be useful in anti-tumour therapy if the indiscriminately-binding B chain could be replaced by a different carrier which has the ability to bind to tumour cells in preference to normal cells. Thus, it has been proposed that an immunotoxin which comprises ricin A and a tumour-specific antibody may be of use in anti-tumour therapy.

The preparation of the A chain of ricin from natural sources, such as from the seeds of *Ricinus communis*, is difficult. In particular it is difficult to purify ricin A, that is to separate the A chain from the B chain.

Although it is possible to prepare polypeptides, such as ricin A, by recombinant DNA technology, there is still a need for improved processes for the preparation of soluble polypeptides. In particular there is a need for improved processes for the preparation of soluble ricin A.

According to the present invention there is provided a process for preparing a polypeptide, which process comprises cultivating a host capable of expressing said polypeptide in a growth medium and:

(a) adjusting the pH of the growth medium during the process, and optionally reducing the temperature of the growth medium during the process; or (b) maintaining the pH at a value which favours growth of the host and reducing the temperature of the growth medium during the process; such that soluble polypeptide may be obtained.

In particular the process of the present invention may be used to prepare polypeptides which have a tendency to be produced, at least in part, in an insoluble form.

Particular examples of polypeptides which may be produced using the present invention include, for example, ricin A or an analogue thereof.

In one embodiment of the present invention there is provided a process for preparing a polypeptide, which process comprises cultivating a host capable of expressing said polypeptide and adjusting the pH during the process such that soluble polypeptide may be obtained. In particular there is provided a method of preparing a polypeptide, which method comprises cultivating a host which is capable of expressing said polypeptide in a growth medium for an initial period at a first pH value which favours growth of the host; adjusting the pH to a second value which favours accumulation of soluble polypeptide and cultivating the host for a further period at said second pH value.

In a further embodiment of the present invention there is provided a process for preparing a polypeptide, which process comprises cultivating a host capable of expressing said polypeptide and reducing the temperature during the process such that soluble polypeptide may be obtained.

In processes where the temperature is reduced, the process will in general comprise cultivating the host cells at a temperature which favours growth of the host cells and generation of soluble polypeptide, cooling growth medium (and hence the host) during the terminal portion of the cultivation, and harvesting the host during said terminal portion.

The temperature is preferably one which favours maintenance of the polypeptide in a soluble form.

Suitable temperatures which favour growth of bacterial cells, such as *E. coli*, are those from about 25° C. to about 39° C. (for example 37° or 38° C.), with the optimum temperature being about 37° C. The temperature should preferably be one which leads to the generation of soluble polypeptide and so, in general, the temperature will be below 40° C. In general, it is preferred that when the temperature is reduced, the host cells are cooled to a temperature below about 25° C., for example to a temperature in the range from about 10° C. (or below) to about 25° C.

It is preferred that cooling is effected at the point where the accumulation of soluble polypeptide (such as ricin A) within the cells is high and most preferably at or near the maximum specific activity.

It is generally preferred that when the pH is adjusted, the host which is capable of expressing the polypeptide is cultivated in a growth medium for an initial period at a first pH value which favours growth of the host, and the pH is adjusted to a second value and the host cultivated for a further period at this second value. The pH may be adjusted in a number of ways, for example it may be adjusted in one step or in a series of steps. The second pH may, for example, comprise a value which favours accumulation of soluble polypeptide in that it facilitates the maintenance and recovery of polypeptide in a soluble form.

Thus in a particular embodiment there is provided a process for preparing a polypeptide, which process comprises cultivating a host capable of expressing said polypeptide at a first pH value and at a temperature which favours growth of the host and generation of soluble polypeptide, adjusting the pH during the process to a second pH value, and optionally cooling the host during the terminal portion of the cultivation, and harvesting the host containing soluble polypeptide during said terminal portion.

In the case of ricin A, the pH is generally adjusted so that the said second pH value will be lower than the first pH value. For other polypeptides the said second pH value may be greater or may be lower than the first value, depending on the nature of the polypeptide.

In a particular embodiment, when the pH is adjusted the value of the pH is changed from a first value to a second value which is lower than the first value. As indicated above, the pH may be lowered in a number of ways, for example it may be lowered in one step or in a series of steps.

It is generally preferred for example, that the pH is adjusted from the first value to the second value over a short period of time, and in particular the pH may be adjusted directly from the first value to the second value.

Particular values for the pH during the initial period of the cultivation include, for example, those in the range of about 6 to 8. A preferred value for the pH during the initial period is, for example, 6.7 or about 6.7. Values of pH which are about 6.7 include, for example, values of $6.7\pm0.1$, and hence include a value of 6.8.

Particular values for the pH during the further period of cultivation are those in the range of about 5.5 to 8, and in particular in the range of about 6 to 8. For example, where the pH during the initial period, that is said first value, is about 6.7, a particular value for the pH during the further period is one which has a value lower than 6.7 and greater than about 5.5 (especially a value greater than, or equal to, about 6.0).

In particular the present invention provides a process for preparing ricin A or an analogue thereof. Thus, according to the present invention there is provided a method of preparing ricin A or an analogue thereof, which method comprises cultivating a host which is capable of expressing ricin A, or an analogue thereof, in a nutrient medium for an initial period at a first pH value which favours growth of the host; and cultivating the host for a further period at a pH lower than said first pH value; and optionally cooling the host during the terminal portion of the cultivation and harvesting the host during said terminal portion.

Analogues of ricin A include polypeptides which exhibit cytotoxic activity and which have a primary structure which is related to ricin A in the sense that it differs from that of ricin A by one or more amino acid alterations (deletions, additions, substitutions) which do not result in loss of cytotoxic activity. The preparation of hosts which are capable of expressing ricin A is described, for example in EP 145,111; WO 85/3508; and Lamb et al. Eur. J. Biochem., 1985, 148, p265–270.

As mentioned above polypeptides which possess cytotoxic properties such as ricin A may be used to prepare immunotoxins for use in treatment of tumours. Generally, such immunotoxins comprise an antibody specific for the tumour to be treated and the toxin. An example of the preparation of an immunotoxin is described in published PCT Patent Application no. WO 85/003508.

It is generally preferred, for example, that the host comprises bacterial cells such as *E. coli* cells. In the case of ricin A it is preferred that the host comprises an *E. coli* strain such as DS410.

The host is generally cultivated in a medium which contains those nutrients which fulfill the cellular growth requirements of the host. Thus the medium will, in general, include sources of carbon and nitrogen for synthesis of cellular components and energy, ions such as sulphate, phosphate, magnesium, calcium, iron and trace elements.

It is preferred that yeast extract is added to the fermentation medium during the course of the fermentation. The modes of addition of the yeast extract include those mentioned below.

The host will include a DNA sequence which codes for the polypeptide (such as ricin A or an analogue thereof) and which is under the control of appropriate control sequences such as a promoter sequence, ribosome binding site and transcription terminator sequence. Particular examples of suitable promoter sequences are the tryptophan (trp) promoter and the T7A3 promoter. Other promoters such as the lac or tac promoter may also be used. Thus, for example, the host may include a DNA sequence which codes for ricin A and which is under the control of the trp or T7A3 promoters.

In a particularly preferred embodiment the process of the present invention comprises a fermentation of the "fed-batch type".

As used herein the term a process of the "fed-batch type" refers to a fermentation process in which the batch growth medium contains a nutrient, such as carbon source, or a number of nutrients that will when exhausted limit the growth of the microorganism. When that nutrient or nutrients become exhausted a feed of that nutrient/nutrients is initiated. The point at which it becomes necessary to feed this nutrient corresponds to the onset of fed-batch conditions. The fermentation medium may be supplied with other nutrients throughout or at stages during the fermentation.

When the process comprises a fed-batch fermentation process the pH may be lowered at or before the point at which fed-batch conditions are attained, preferably before fed-batch conditions are attained.

In a preferred embodiment there is provided a fermentation process of the fed-batch type for preparing ricin A, which process comprises cultivating an *E. coli* host which is capable of expressing ricin A at a pH value of about 6.7 for an initial period and cultivating the host for a further period at a pH lower than said value of 6.7.

According to a preferred embodiment of the present invention there is provided a fermentation process of the fed-batch type for preparing ricin A or an analogue thereof, which process comprises cultivating a host capable of expressing ricin A, or an analogue thereof, in a growth medium for an initial period at a first pH value and at a temperature which layouts growth of the host and generation of soluble ricin A or ricin A analogue; adjusting the pH before fed-batch conditions are attained to a second value which is lower than said first value; and optionally cooling the growth medium during the terminal portion of the cultivation to a temperature which favours maintenance of ricin A in a soluble form and harvesting the cells during said terminal portion.

Prior to implementation of the processes claimed in this application it was found that fermentation processes of the fed-batch type resulted in decreased yields of soluble ricin A recoverable at the end of the fermentation process. It has been surprisingly discovered that if cooling is effected before fed-batch conditions are attained then high levels of polypeptide may be maintained in soluble form, thus facilitating harvesting of soluble polypeptide.

Thus in a further embodiment of the present invention there is provided a process for preparing ricin A or an analogue thereof, which process comprises (a) cultivating a host capable of expressing ricin A, or an analogue thereof, in a growth medium at a temperature which favours growth of the host and generation of soluble ricin A or ricin A analogue;

(b) cooling the growth medium before exhaustion of a nutrient essential for growth of the host is reached (that is fed-batch conditions are attained) to a temperature which does not favour growth of the host; and (c) harvesting the cells before exhaustion of said nutrient is reached.

It will be appreciated that this process is similar to a fed-batch process in which harvesting takes place before the process enters the fed-batch phase. Thus the point at which exhaustion of a nutrient essential for growth of the host occurs is equivalent to the point at which fed-batch conditions are attained. Cooling is effected before nutrient exhaustion is reached, and preferably takes place, for example, just before or immediately before nutrient exhaustion is reached.

The host may be grown in a medium which is formulated to become carbon-limited at an $OD_{550}$ of about 50, and the fermentation medium containing the host is cooled when the $OD_{550}$ is about 50 or before the $OD_{550}$ reaches 50.

In particular when it is desired to reduce the temperature in a fed-batch process for the preparation of ricin A, the process may include the steps of:

(a) cultivating a *E. coli* host capable of expressing ricin A in a nutrient medium at a temperature of in the range from about 37° C. to about 39° C.;

(b) cooling the fermentation medium before fed batch conditions are attained to a temperature below about 25° C.; and (c) harvesting the host cells before fed-batch conditions are attained.

Examples of particular temperatures are those mentioned above. Thus cooling may be to a temperature in the range from about 10° C. (or below) to about 25° C.

According to the present invention there is also provided a method of preparing ricin A, or an analogue thereof, said method comprising cultivating a host capable of expressing ricin A, or an analogue thereof, in a growth medium and adding a supplement which includes yeast extract to the growth medium during the cultivation.

The yeast extract may be added by way of a single batch, a series of aliquots or a substantially continuous feed. The yeast extract will, in general, be added during the growth phase of the host. It is preferred, for example, that addition of the supplement which includes yeast extract is initiated at a predetermined time after the start of the cultivation. A particular example of this time is a point which is before fed-batch conditions are attained.

The rate of addition of the supplement which comprises yeast extract is preferably such that the growth medium does not become exhausted of yeast extract. Thus if the initial composition of the growth medium includes yeast extract then the addition of the supplement is preferable initiated before the yeast extract present in the initial composition has been consumed. Suitable rates of yeast extract feed include, for example, feed rates in the range of about 0.85 to 3.4 $g.l^{-1}h^{-1}$. A particular rate of feed is one in the range 1 to 2 $g.l^{-1}h^{-1}$, more particularly 1.7 $gl^{-1}h^{-1}$.

As mentioned above, the host cells may, in general, comprise bacterial cells, such as *E. coli*; and it is preferred, for example, that the host cells are capable of expressing ricin A.

The fermentation is generally carried out at a temperature which favours growth of the host. A particularly suitable temperature which favour growth of bacterial cells, such as *E. coli*, is about 37° C. The temperature may be reduced during the cultivation (especially during the terminal portion of the cultivation) as mentioned above.

According to a preferred embodiment of the present invention there is provided a process of the fed-batch type for preparing ricin A or an analogue thereof, which process comprises cultivating a host capable of expressing ricin A or an analogue thereof in a growth medium, and adding a supplement which includes yeast extract to the growth medium before the point at which fed-batch conditions are attained.

It has also been found that *E. coli* strain DS410 is surprisingly efficient at producing soluble ricin A. Thus the present invention also provides a process for the preparation of ricin A, which process comprises cultivating a host capable of expressing ricin A and in which the host comprises *E. coli* DS410. Also as mentioned above, it is generally preferred that the pH is adjusted and/or the temperature reduced.

After harvesting, the cells are processed to recover the ricin A. This processing will normally involve disrupting the cells, separating the crude ricin A polypeptide from other proteinaceous material by one or more extraction steps and further purifying the ricin A by gel filtration, high performance liquid chromatography or other conventional purification techniques.

The processes of the present invention have been found to be advantageous in the preparation of soluble polypeptides.

In general the processes of the present invention are advantageous in the generation and/or recovery of polypeptides in a soluble form. In particular it has been found that high yields of soluble polypeptide may be obtained by adjusting the pH of the growth medium during the process. It has also been unexpectedly found that if the growth medium is cooled during the terminal portion of the cultivation and the cells harvested during this terminal portion, then high yields of soluble polypeptide may be recovered. This cooling step has been found to be particularly advantageous since it leads to greater process latitude in that high yields of soluble polypeptide may be obtained even if there is a delay before harvesting. Fed-batch processes in which the pH is adjusted and an optional cooling step is effected have been found to be particularly advantageous.

In processes where the polypeptide is ricin A, the processes of the present invention have been found to be particularly advantageous.

The yields of soluble ricin A obtained have been found to be enhanced if yeast extract is added during the process. Processes in which the pH is also been adjusted, and especially fed-batch processes in which the pH is adjusted have been unexpectedly found to give high yields of soluble ricin A.

Also *E. coli* DS410 has been unexpectedly found to be advantageous in the preparation of soluble ricin A. It has also been found that the yield is enhanced if yeast extract is added during the process.

The invention will now be further described, by way of example only, with reference to the accompanying Examples and drawings in which.

Figure 8:
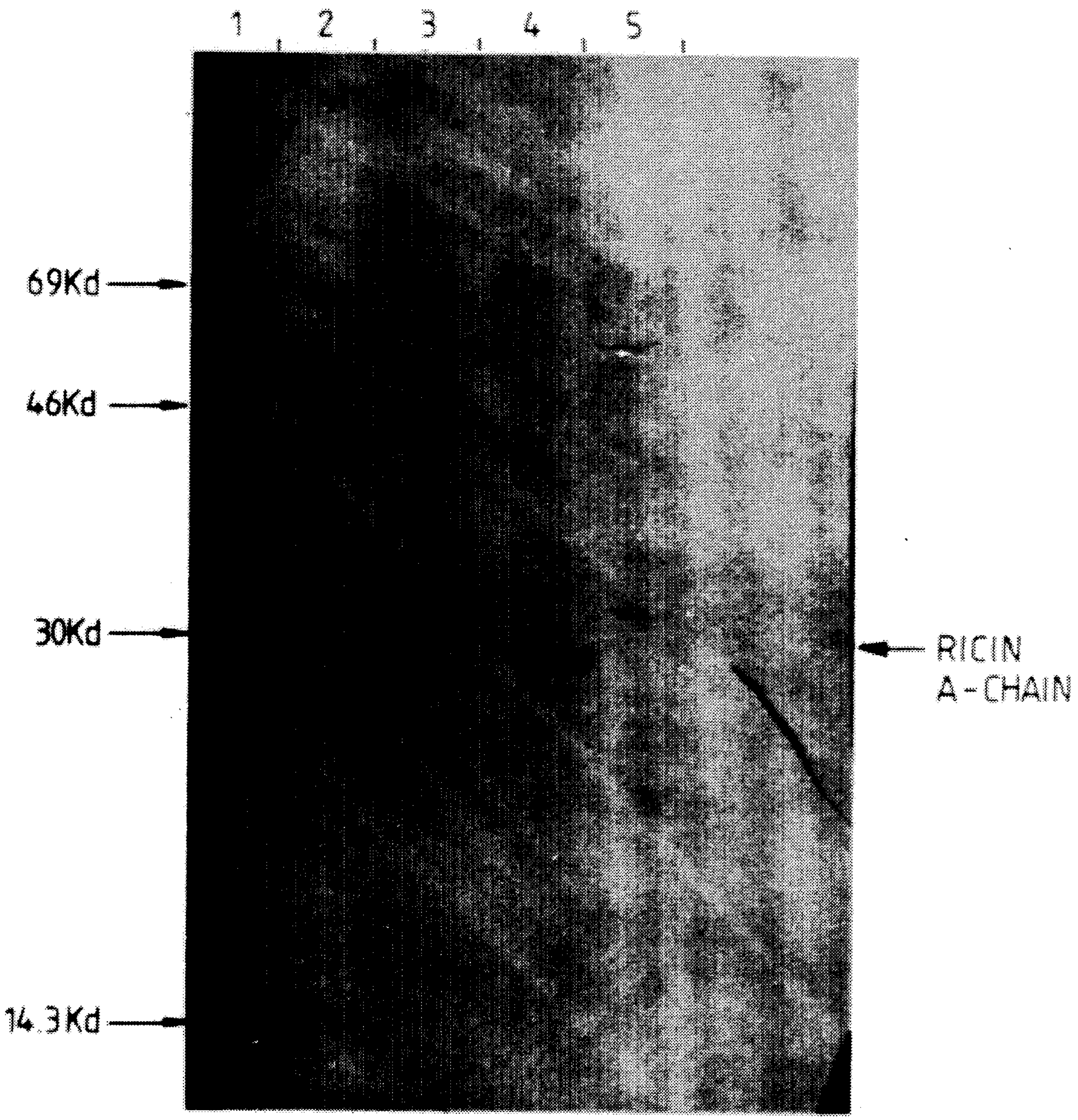
Figure 10A:
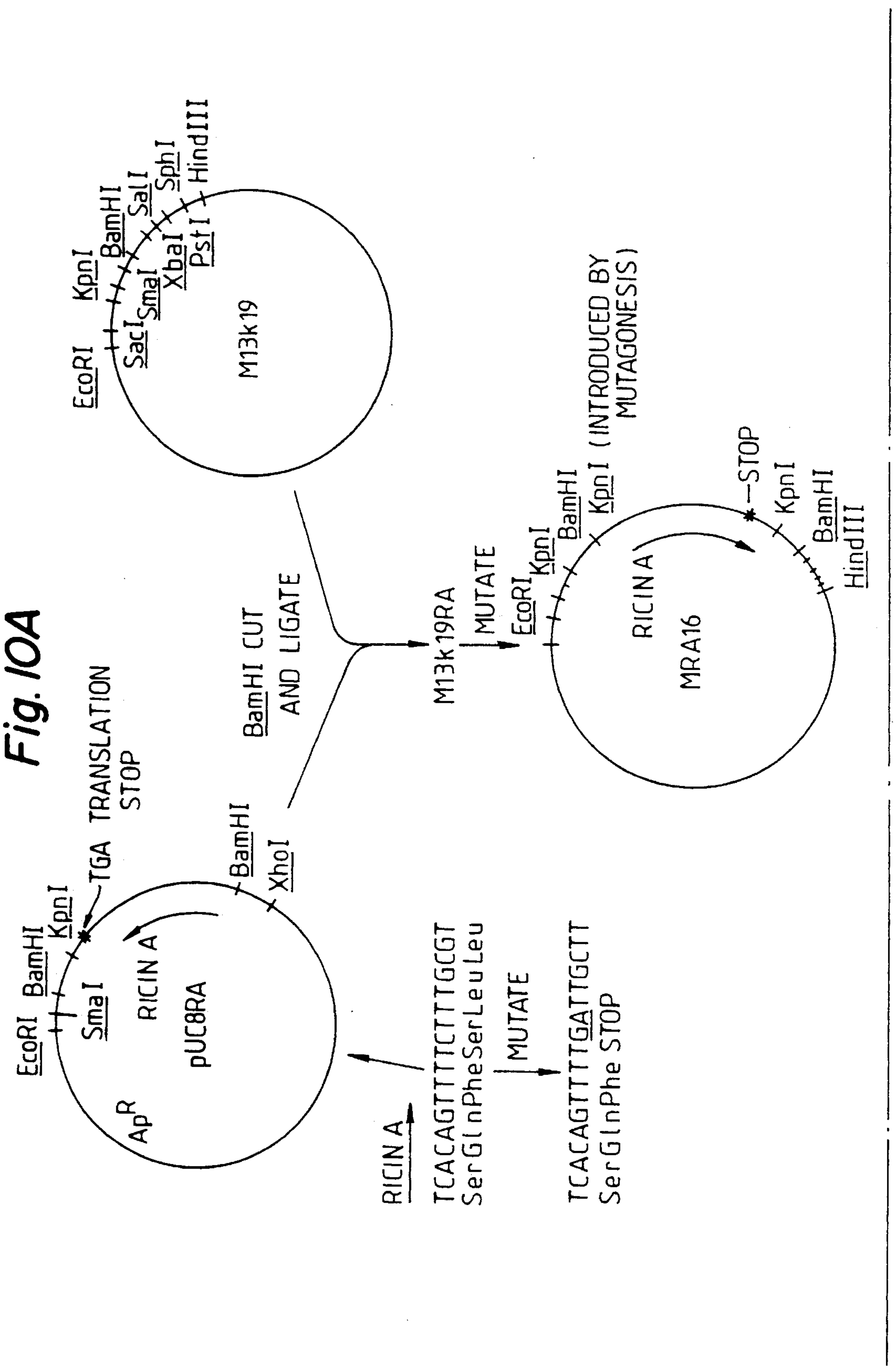
Figure 10B:
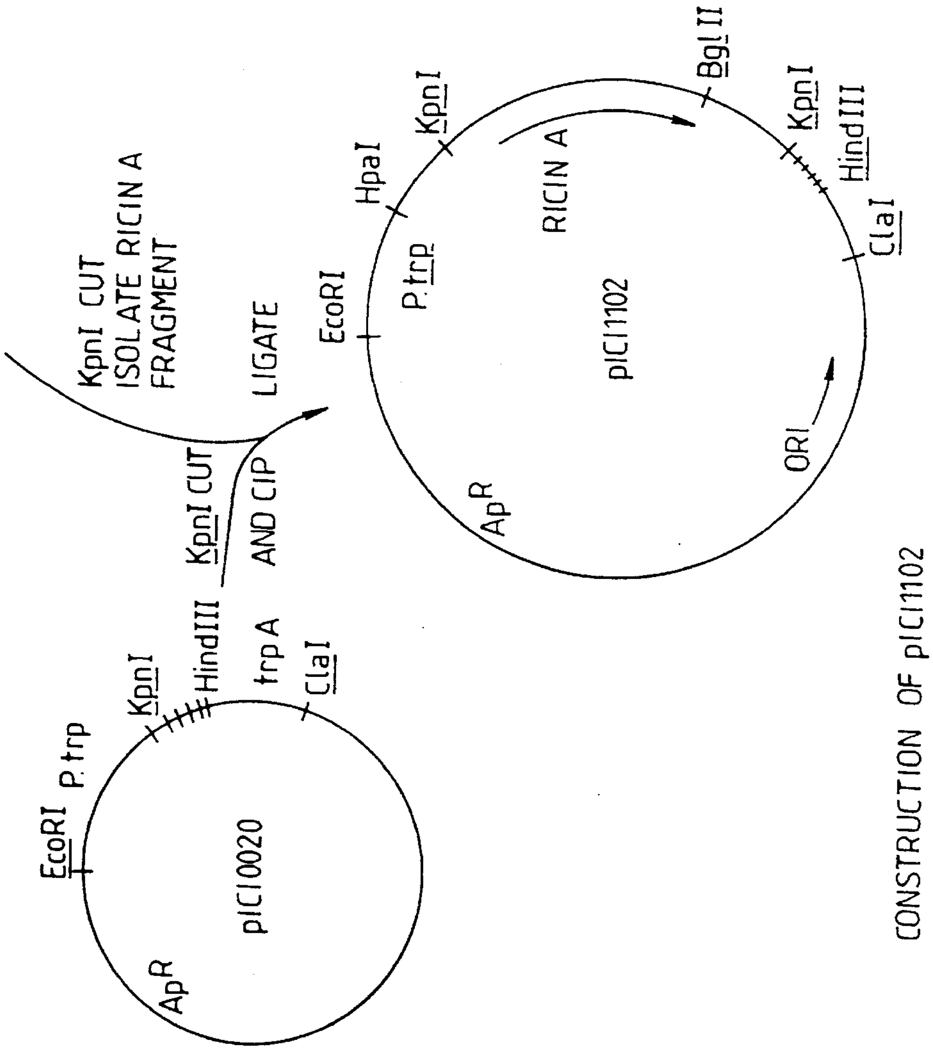
Figure 12:
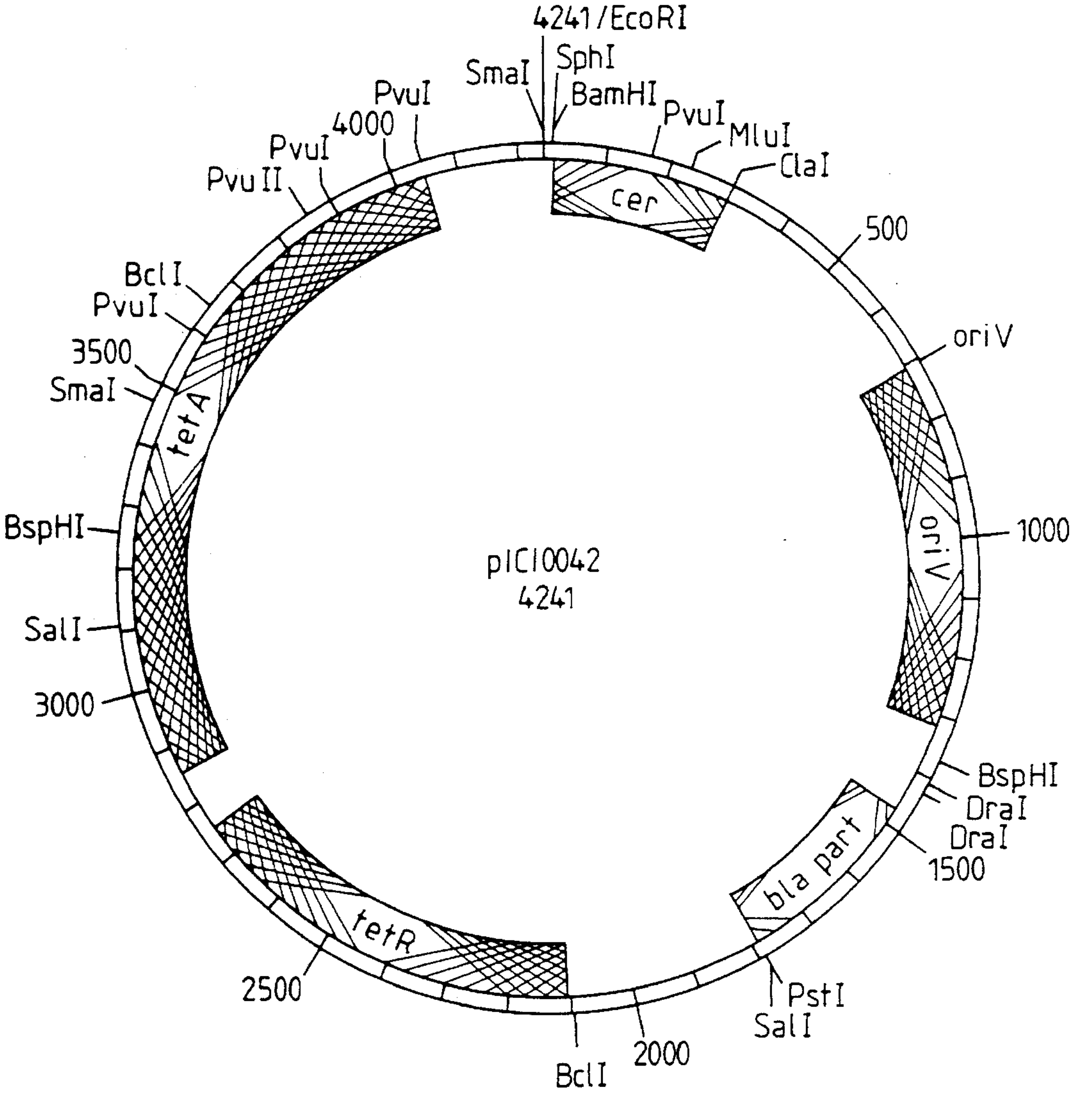
Figure 14:
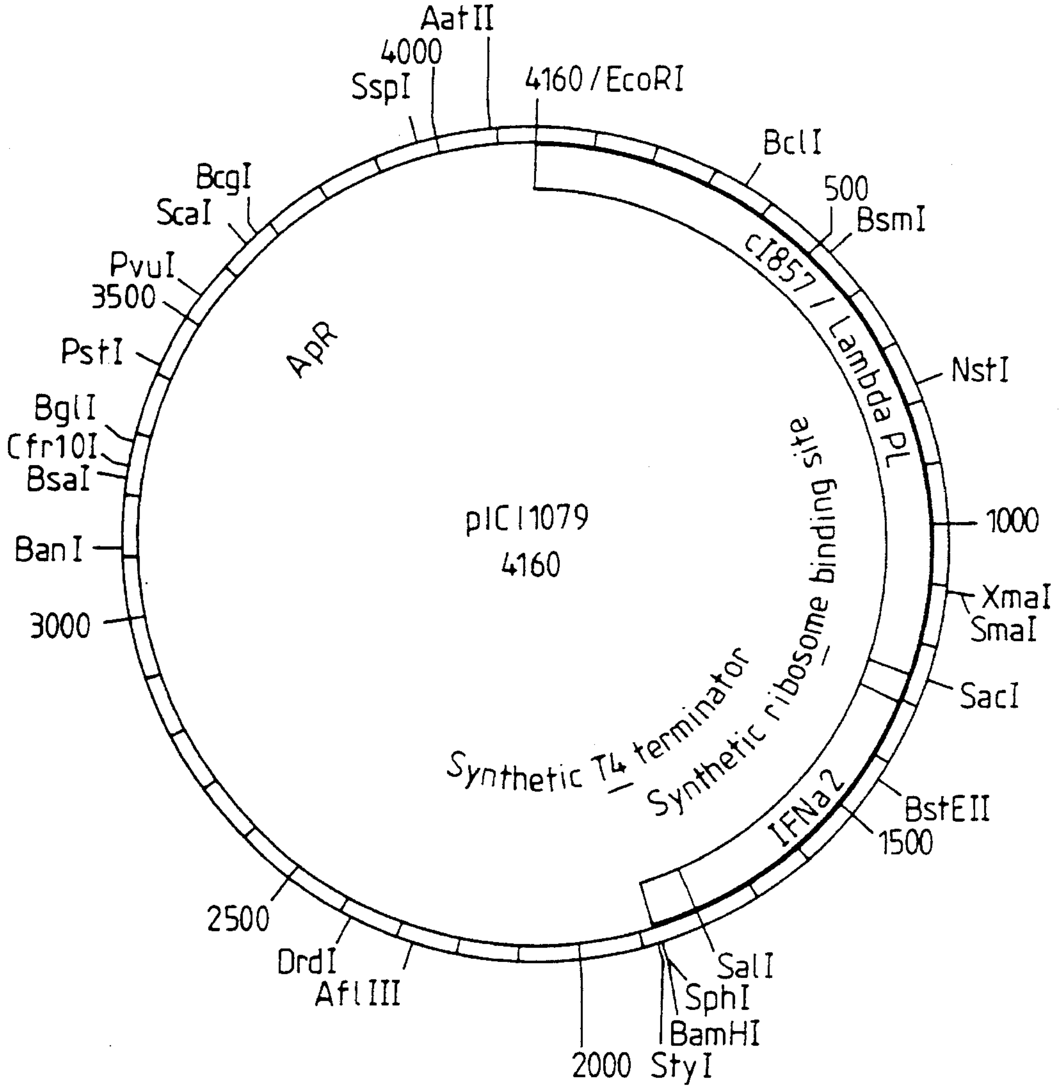
Figure 16:
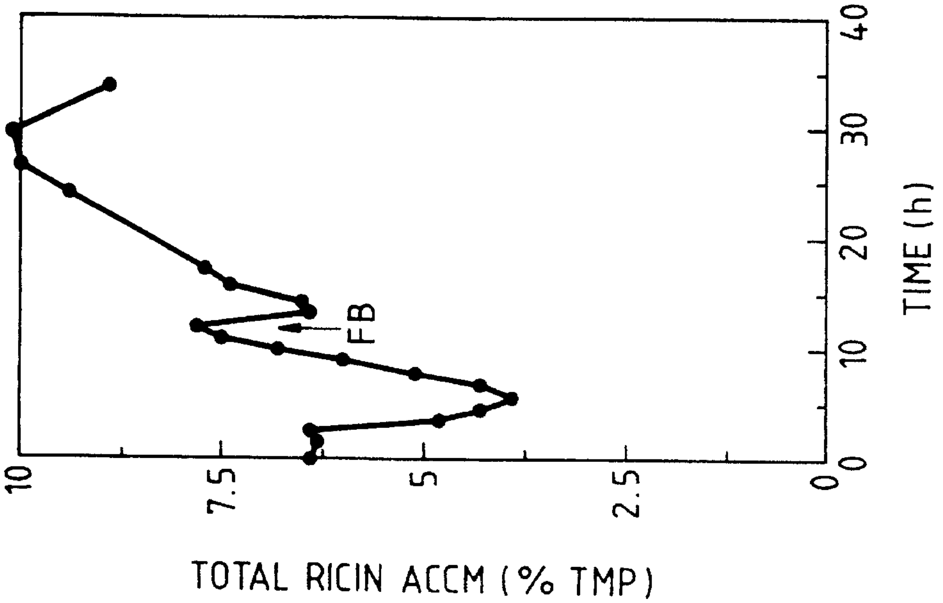
Figure 15:
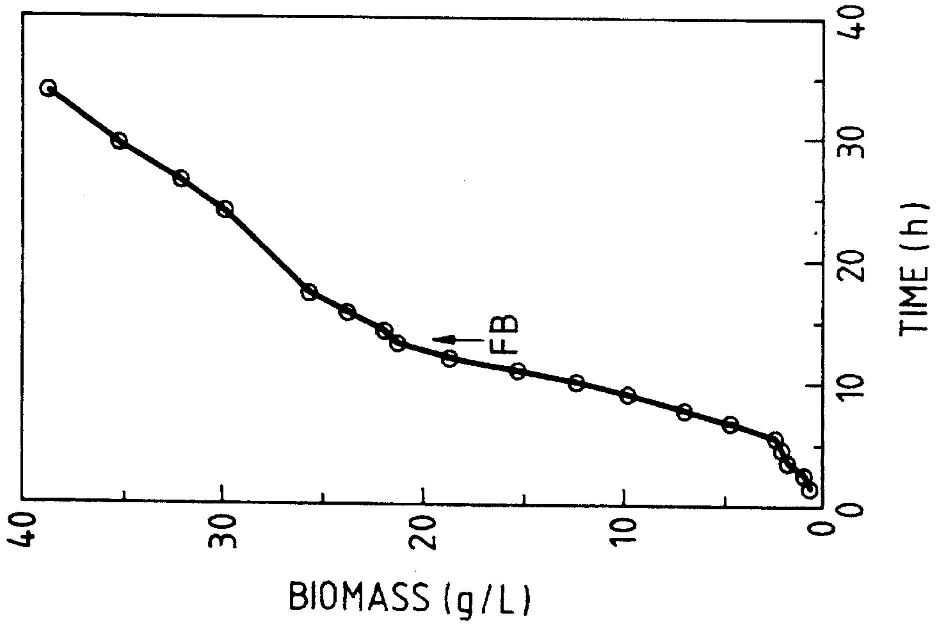
Figure 18:
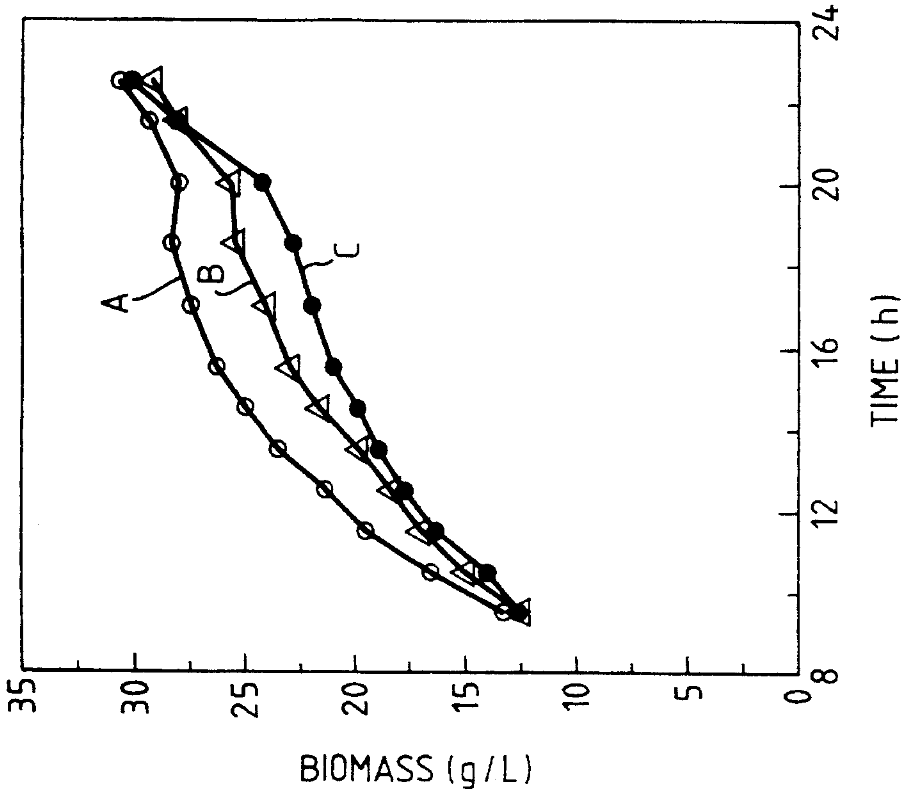

FIG. 8 is a western blot of ricin A produced by pICI 1102 and in which track 1 is molecular weight markers; 2 and 3 are non-ricin producing clones; 4 is pICI 1102, and 5 is pICI 0020 (control plasmid-non ricin A sequence);

FIG. 9 is a partial sequence of pICI 1102 (SEQ ID NOS:15 and 16);

FIG. 10 illustrates the construction of pICI 1102 (SEQ ID NOS:17, 18, 19 and 20);

FIG. 11 describes a fragment (SEQ ID NO:21) used in the preparation of plasmids;

FIG. 12 is a plasmid map of pICI 0042;

FIG. 13 illustrates the sequence of a transcription terminator (SEQ ID NOS:22 and 23);

FIG. 14 is a plasmid map of pICI 1079;

FIGS. 15, 16 and 17illustrate the effect of fed batch fermentation on biomass, total ricin A accumulation and ricin A partitioning in the soluble fraction respectively for DS410;

FIGS. 18, 19, 20 and 21 illustrate the effect of different pH control regimes on biomass concentration, total ricin A accumulation, percentage of soluble ricin A partitioning in the soluble fraction, and the yield of soluble ricin A respectively.

Figure 22:
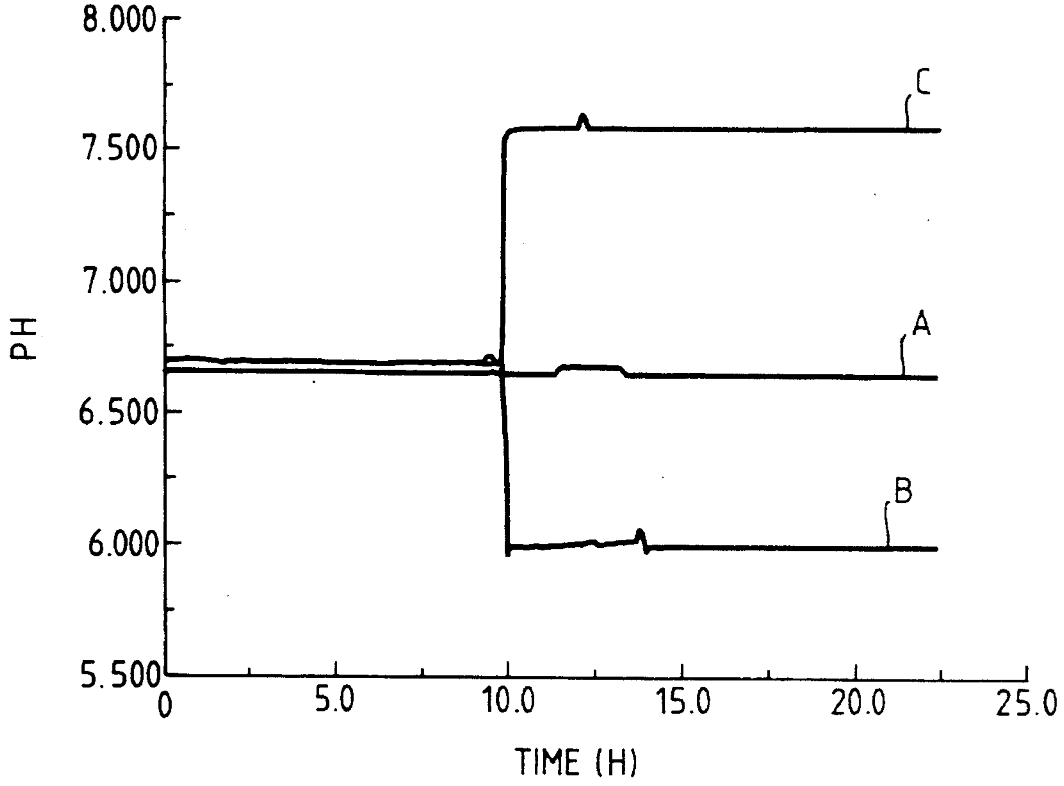

FIG. 22 illustrates the pH profiles employed; and

Figure 24:
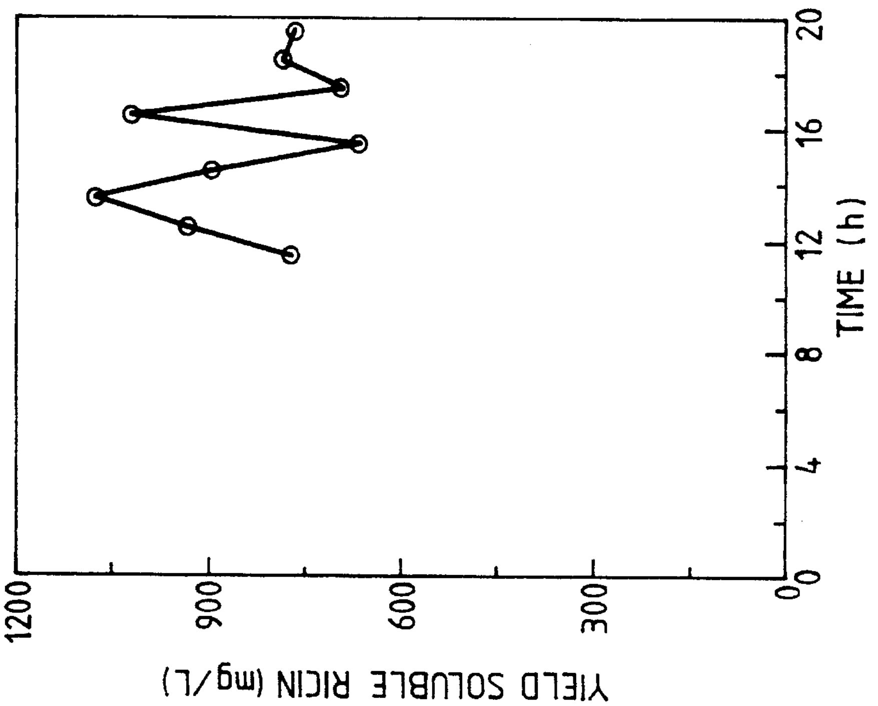
Figure 23:
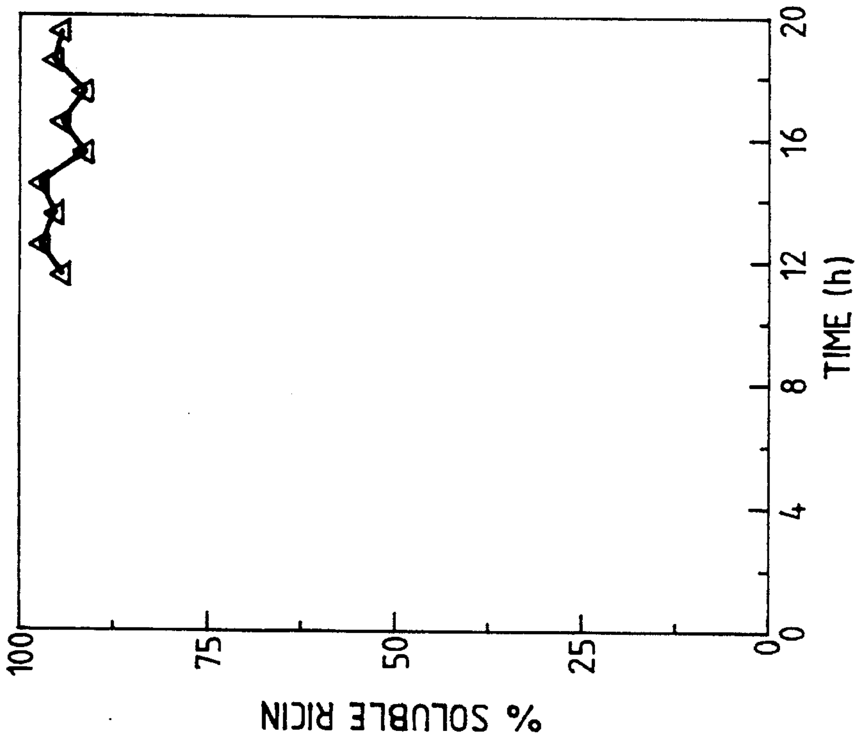
Figure 25:
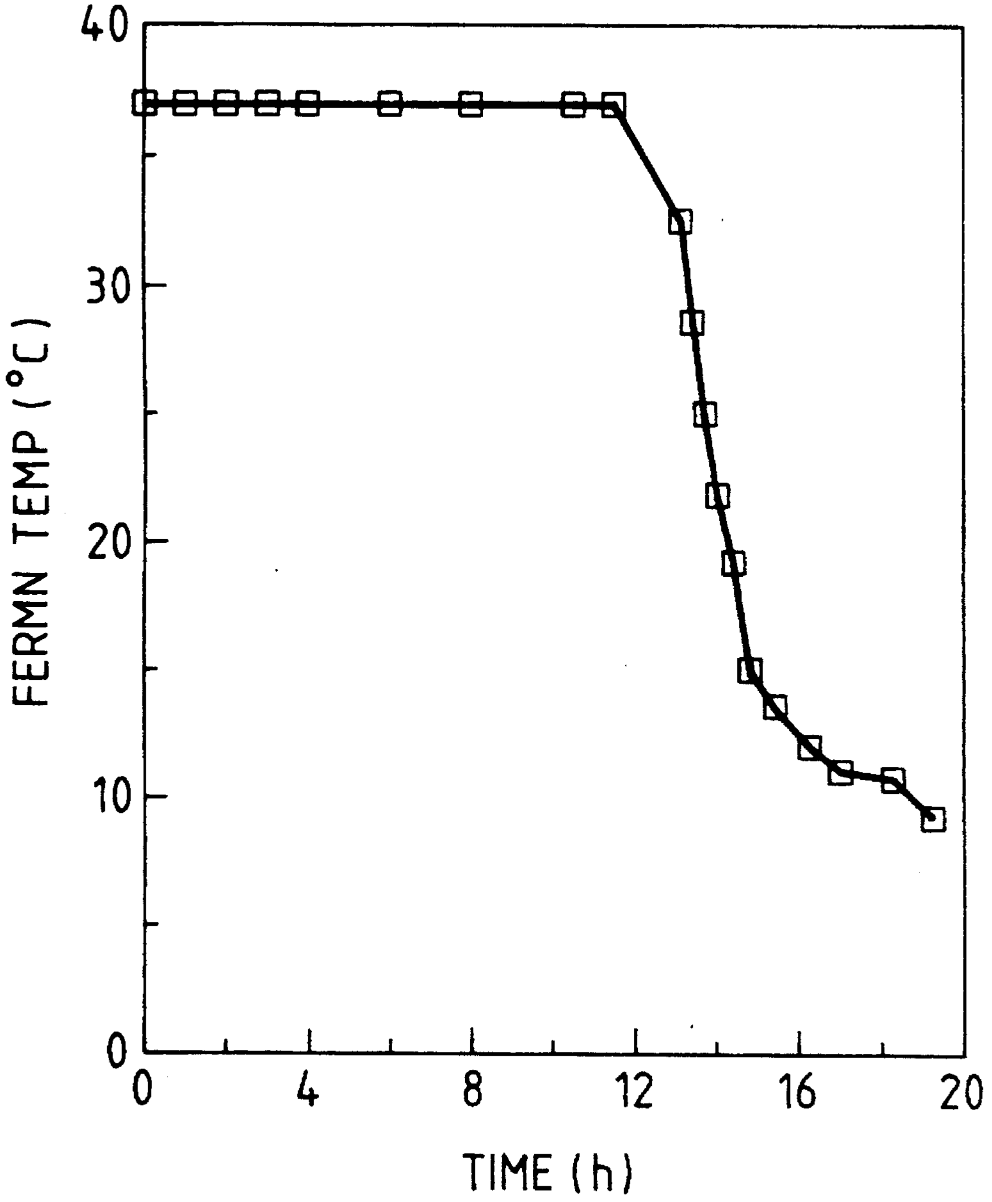

FIGS. 23, 24 and 25 illustrate the effect of cooling.

Growth Medium

| Composition of LCM50 | Made up of distilled water g/l |
|---|---|
| $KH_2PO_4$ | 3.0 |
| $Na_2HPO_4$ | 6.0 |
| NaCl | 0.5 |
| Casein Hydrolysate (Oxoid L41) | 2.0 |
| $(NH_4)_2SO_4$ | 10.0 |
| Yeast Extract (Difco) | as specified |
| Glycerol | 35.0 |
| $MgSO_4.7H_2O$ | 0.5 |
| $CaCl_2.2H_2O$ | 0.03 |
| Thiamine | 0.008 |
| $FeSO_4$/Citric Acid | 0.04/0.02 |
| Trace element solution (TES) | (0.5 ml $l^{-1}$) |
| Tetracycline | (10 mg $l^{-1}$) |

The concentration of yeast extract in the LCM50 growth medium is specified in each Example.

The trace element solution (TES) has the following composition:

| | mg/10 ml deionised water |
|---|---|
| $AlCl_3.6H_2O$ | 2.0 |
| $CoCl_2.6H_2O$ | 0.8 |
| $KCr(SO_4)_2.12H_2O$ | 0.2 |
| $CuCl_2.2H_2O$ | 0.2 |
| $H_3BO_3$ | 0.1 |
| KI | 2.0 |
| $MnSO_4.H_2O$ | 2.0 |
| $NiSO_4.6H_2O$ | 0.09 |
| $Na_2MoO_4.2H_2O$ | 0.4 |
| $ZnSO_4.7H_2O$ | 0.4 |

Strains

The *E. coli* strains referred to herein are freely available. For example, *E. coli* MM294, and W3110 are freely available. MM294 and W3110 may, for example be obtained from the *E. coli* Genetic Stock Centre, Yale University, USA. Δlac derivatives of W3110 are readily produced by those experienced in the art. *E. coli* DS410 is well known (Dougan and Sherratt, Molecular and General Genetics, Vol 151, p151–160, 1977) and has the published genotype $F^-$ ara azi ton A lac Y min A min B rps L mal A xyl mtl thi. This strain is freely available to the public, and moreover was deposited by the Applicants on 7 Jun. 1985, under the Budapest Treaty, with the National Collections Of Industrial & Marine Bacteria Ltd, Aberdeen, Scotland under deposition number 12100.

EXAMPLE 1

*E. coli* strains MM294, DS410, and a Δlac derivative of W3110 termed W3110Δlac were transformed with pICI 1187.

The resultant strains MM294 (pICI 1187), DS410 (pICI 1187) and W3110Δlac (pICI 1187) were purified and maintained in glycerol stocks at −80° C. Aliquots of each culture were removed from stock and streaked onto agar plates of L-tetracycline to separate single colonies after overnight growth at 37° C.

Single colonies of DS410 (pICI 1187) W3110Δlac (pICI 1187) and MM294 (pICI 1187) were removed, separately resuspended in a 10 ml L-tetracycline broth and 100 μl immediately inoculated into each of ten 250 ml Erlenmeyer flasks containing 75 ml of L-tetracycline broth. After growth for 16 h at 37° C. on a reciprocating shaker the contents of the flasks in each set of ten were pooled and used to inoculate three separate fermenters containing LCM50 (10g/l yeast extract).

Fermentations were carried out at a temperature of 37° C. and pH, controlled by automatic addition of 2M sulphuric acid and 6M sodium hydroxide solution, of pH6.7. The dissolved oxygen tension (dOT) set point was 50% air saturation and was initially controlled by automatic adjustment of the fermenter stirrer speed. Airflow to the fermenters was 20 L/min corresponding to 1 volume volume per minute (VVM) throughout.

Fermentations were performed for 14.25 hours and during that time samples were taken for measurement of optical density ($OD_{550}$), cell dry weight, accumulation and partitioning of ricin A within the cells. Ricin A accumulation was measured by scanning Coomassie blue stained SDS-PAGE gels of whole cell lysates of the sampled bacteria as is well known in the art. Partitioning of ricin A in the cytoplasmic (soluble) and inclusion body (insoluble) fractions of cells was determined by subjecting sampled bacteria to sonication lysis as is well known in the art.

Changing the *E. coli* host strain for plasmid pICI 1187 produced an unexpected change in the level of ricin A partitioned in the soluble cytoplasmic fraction. Table 1 illustrates the biomass yield, total ricin A accumulation and percentage of ricin A partioning in the soluble fraction at the end of the fermentation (14.25 hours) for strains DS410 (pICI 1187), W3110Δlac (pICI1187) and MM294(pICI 1187).

TABLE 1

| STRAIN | BIOMASS $gl^{-1}$ | TOTAL RICIN A ACCUMU-LATION % TMP* | % RICIN A PARTITIONING IN SOLUBLE FRACTION |
|---|---|---|---|
| DS410 (pICI 1187) | 9.3 | 5.9 | >80 |
| W3110Δlac (pICI 1187) | 14.4 | 7.5 | ca. 40 |
| MM294 (pICI 1187) | 10.4 | 7.6 | ca. 40 |

*TMP means total microbial protein.

It is evident that by changing the *E. coli* host strain dramatic changes in ricin A partitioning can be produced.

EXAMPLE 2

The fermentation process described in Example 1 was repeated with LCM50 growth medium (20g/l yeast extract) using strains DS410 (pICI 1187), W3110Δlac (pICI 1187) and MM294 (pICI 1187). A solution of yeast extract (333 $gl^{-1}$) was fed into the fermenters from 4.25 h post fermenter inoculation at $0.85gl^{-1}h^{-1}$. The yeast extract feed rate was increased to $1.7gl^{-1}h^{-1}$ 5.75 h post fermenter inoculation. When the carbon source in the fermentations became exhausted (leading to a rapid rise in dOT), a feed containing glycerol ($714gl^{-1}$) and ammonium sulphate ($143gl^{-1}$) was pumped into the fermenters at a rate which restricted bacterial oxygen uptake rate.

Except for the elevated batch yeast extract concentration and the supply of yeast extract solution during fermentation, the medium and fermentation conditions for the three fermenters were identical to the process described in Example 1.

The fermentation process described in this example resulted in an improvement in biomass of all 3 strains, an improvement in the amount of ricin A which was partitioned in the soluble fraction of strains W3110Δlac (pICI 1187) and MM294 (pICI 1187) and an improvement in the total yield of soluble ricin A of all strains compared to Example 1. Table 2 shows the final biomass concentrations, total ricin A accumulation, percentage of ricin A partitioning in the soluble fraction and calculated yields of soluble ricin A at the end of the fermentations (16.25 hours).

TABLE 2

| STRAIN | BIO-MASS $gl^{-1}$ | TOTAL RICIN A ACCUMU-LATION (% TMP) | % RICIN A PARITION-ING IN SOLUBLE FRACTION | YIELD SOLUBLE RICIN A $mgl^{-1}$* |
|---|---|---|---|---|
| DS410 (pICI1187) | 24.3 | 7.0 | 80 | ca 600(1) |
| W3110Δlac (pICI1187) | 23.1 | 8.4 | 60 | ca 600(1) |
| MM294 (PICI1187) | 19.3 | 9.7 | 50 | ca 400(1) |

*calculated yield mg soluble ricin A per litre fermentation broth.
(1)compared to calculated yields of soluble ricin A for the three strains in the fermentation processes described in Example 1 of ca 150–200 $mgl^{-}$.

Similar results were obtained when the yeast extract concentration in LCM50 was 10 g/L and yeast extract was fed into the fermentor and/or when yeast extract was pumped into the fermenter at 0.85 $gl^{-1}h^{-1}$, 1.7 $gl^{-1}h^{-1}$ or 3.4 $gl^{-1}h^{-1}$ throughout.

Yeast extract feeding is thus able to increase the % of ricin A partitioning in the soluble fraction and the yield of soluble ricin per liter of fermentation broth.

EXAMPLE 3

The fermentation process of Example 1 was repeated with *E. coli* strains MM294 (pICI 1187), W3110Δlac (pICI 1187) and DS410 (pICI 1187) using LCM 50 (10g/l yeast extract) supplemented with 100 $mgl^{-1}$ of L-tryptophan. An L-tryptophan solution (10 $gl^{-1}$) was pumped into the fermenters at 90 $mgl^{-1}h^{-1}$ throughout the fermentations.

Table 3 compares the biomass concentration, total ricin A accumulation and percentage of ricin A partitioning in the soluble fraction at the end of the fermentation (14.25 h) for the three strains. The supplement and feeding of L-tryptophan was carried out to influence the activity of the tryptophan promoter as is well known in the art. Compared with the fermentation process described in Example 1 and particularly Example 2 a detrimental effect was generally observed. Strain MM294 (pICI 1187) produces higher biomass levels but the percentage of ricin A partitioning in the soluble fraction is decreased. Strains DS410 (pICI 1187)) and W3110Δlac (pICI 1187) show no change in ricin A partitioning but the level of biomass produced is decreased. The results achieved with yeast extract described in Example 2 are thus most surprising since the added yeast extract contains large amounts of tryptophan.

TABLE 3

| STRAIN | BIOMASS $gl^{-1}$ | TOTAL RICIN A ACCUMU-LATION (% TMP) | % TOTAL RICIN A PARTITIONING IN SOLUBLE FRACTION |
|---|---|---|---|
| DS410 (pICI1187) | 7.6 | 6.8 | >80 |
| W3110Δlac (pICI1187) | 11.0 | 7.2 | ca. 40 |

TABLE 3-continued

| STRAIN | BIOMASS $gl^{-1}$ | TOTAL RICIN A ACCUMULATION (% TMP) | % TOTAL RICIN A PARTITIONING IN SOLUBLE FRACTION |
|---|---|---|---|
| MM294 (pICI1187) | 20.8 | 7.2 | ca. 20 |

EXAMPLE 4

The fermentation process of Example 2 was repeated with *E. coli* strain DS410 (pICI 1187) in LCM50 (20 g/l yeast extract).

The fermentation was carried out at a temperature of 37° C. and pH, controlled by automatic addition of 2M sulphuric acid and 6M sodium hydroxide solution, of pH 6.7. The dissolved oxygen tension (dOT) set point was 50% air saturation and was initially controlled by automatic adjustment of the fermenter stirrer speed. Air flow to the fermenter was initially 20 L/min corresponding to 1 volume volume per minute (VVM) and was increased manually to 45 L/min when the fermenter stirrer speed reached its maximum. The fermentation was performed for 34 hours and during that time samples were taken for measurement of optical density ($OD_{550}$), cell dry weight, accumulation and partitioning of ricin A within the bacterial cells. Ricin A accumulation was measured by scanning Coomassie blue stained SDS-PAGE gels of whole cell lysates of the sampled bacteria as is well known in the art. Partitioning of ricin A in the cytoplasmic (soluble) and inclusion body (insoluble) fractions of cells was determined by subjecting sampled bacteria to sonication lysis as is well known in the art. A solution of yeast extract (333 $gl^{-1}$) was pumped into the fermenter 4.5 hours post inoculation at 1.7 $gl^{-1}h^{-1}$.

Between 12–13 hours post inoculation the supply of carbon-source in the fermentation became exhausted leading to a rapid rise in dOT from 50% air saturation. From this point, a feed containing glycerol (714 $gl^{-1}$) and ammonium sulphate (143 $gl^{-1}$) was pumped into the fermenter at a rate which restricted the bacterial oxygen uptake rate (OUR) to approximately 80% of the fermenter's maximum oxygen transfer rate (OTR) whilst returning and then maintaining the dOT at 50% air saturation.

Figure 17:
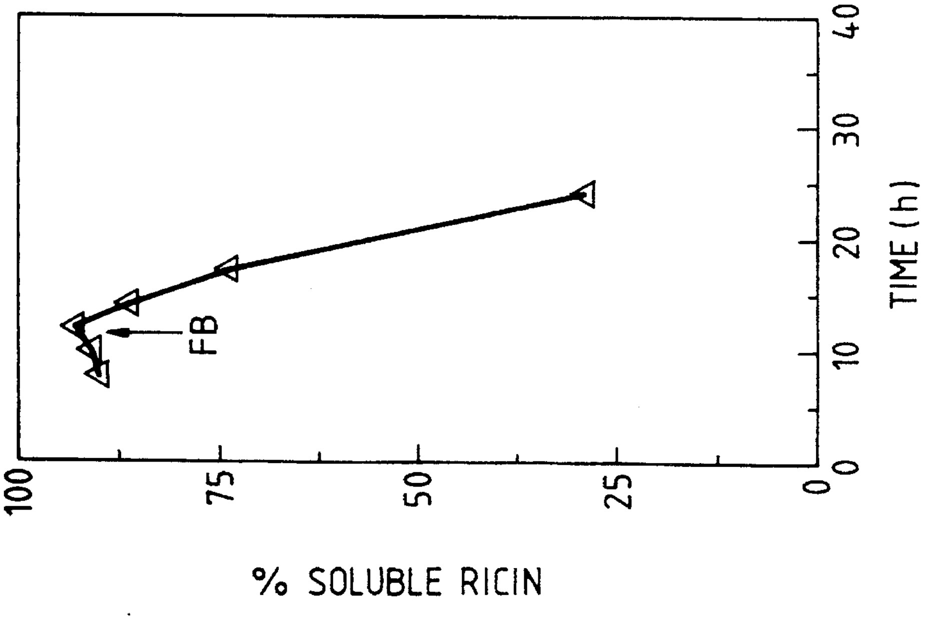
Figure 20:
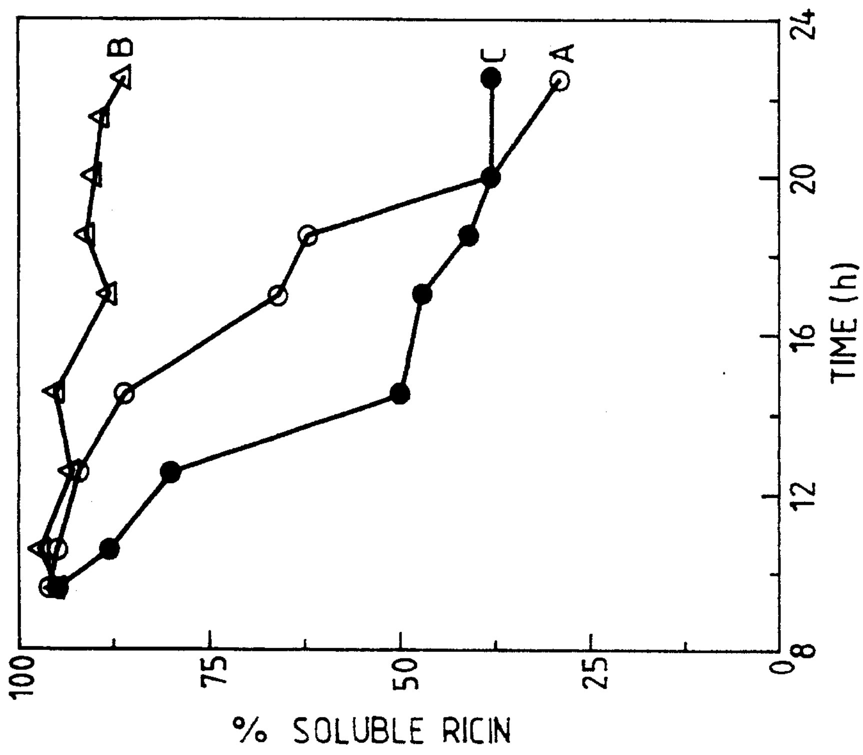
Figure 19:
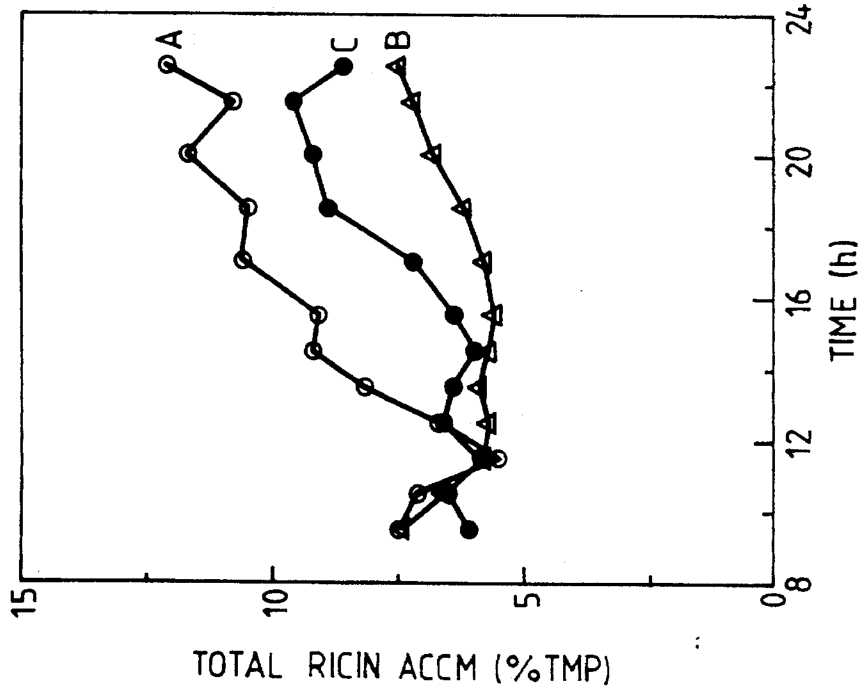
Figure 21:
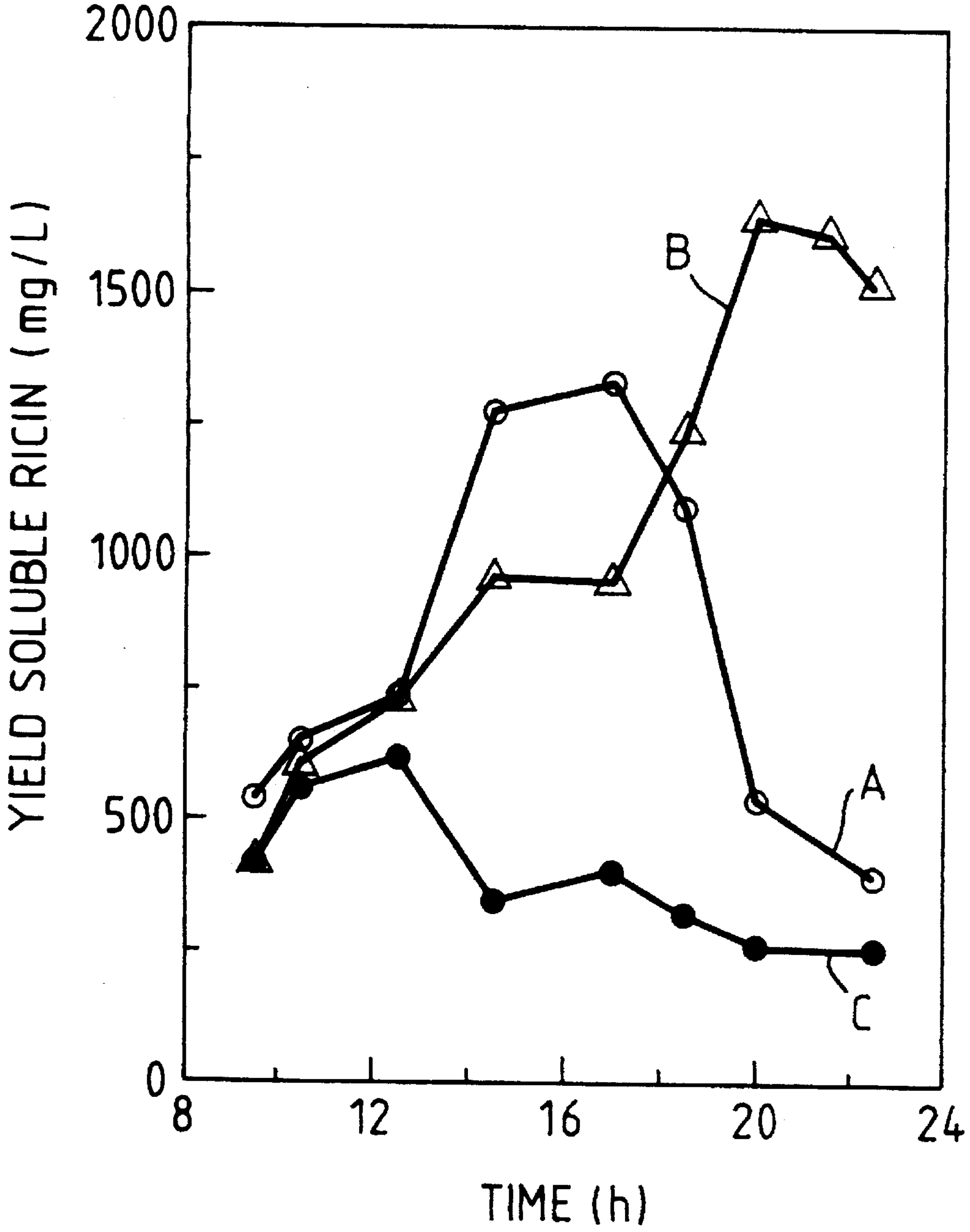

The influence of fed-batch fermentation on biomass production, total ricin A accumulation and ricin partitioning in the soluble fraction is illustrated in FIGS. 15, 16 and 17 respectively. The point at which fed-batch fermentation commences is indicated on each figure (FB). The effect of fed-batch fermentation on ricin portioning in the soluble fraction is clear.

EXAMPLE 5

A single vial of DS410 (pICI 1187) was removed from stock and 100 μl of the culture removed and immediately inoculated into each of three 2 liter Erlenmeyer flasks containing 600 ml of L-tetracycline broth. After growth for 16 h at 37° C. on a reciprocating shaker the contents of the flasks were used to inoculate three fermenters containing LCM50 growth medium (20 g/l yeast extract).

The fermentations were carried out at a temperature of 37° C. and pH, controlled by automatic addition of 2M sulphuric acid and 6M sodium hydroxide solution, of:

(A) pH 6.7 throughout the fermentation (B) pH 6.7 up to 10 h post inoculation, thereafter controlled at pH6.0

(c) pH 6.7 up to 10 h post inoculation, thereafter controlled at pH7.6

The dissolved oxygen tension (dOT) set point was 50% air saturation and was initially controlled by automatic adjustment of the fermenter stirrer speed. Air flow to the fermenters was initially 20 L/min corresponding to 1 volume volume per minute (VVM) and was increased manually to 45 L/min when the fermenter stirrer speed reached its maximum (1000 rpm). The air flow to the fermenters was decreased manually back to 20 L/min when, towards the later stages of the fermentations, the stirrer speed had automatically decreased to approximately 500 rpm.

The fermentations were performed for 23 h and during that time samples were taken for measurement of optical density (0D550), cell dry weight, total ricin A accumulation and ricin partitioning in the soluble fraction. Ricin A accumulation was measured by scanning Coomassie blue stained SDS-PAGE gels of whole cell lysates of the sampled bacteria as is well known in the art. Partitioning of ricin A in the cytoplasmic (soluble) and inclusion body (insoluble) fractions of cells was determined by subjecting sampled bacteria to sonication lysis as is well known in the art.

A solution of yeast extract (333 $gl^{-1}$) was fed into the fermenters from 4.5 h post inoculation at $1.7gl^{-1}h^{-1}$.

When the carbon source in the fermentations became exhausted (leading to a rapid rise in dOT from 50% air saturation) a feed containing glycerol (714 $gl^{-1}$) and ammonium sulphate (143 $gl^{-1}$) was pumped into the fermenters at a rate sufficient to meet the maximum carbon demand of the bacteria. The feed rate of the limiting carbon source and ammonium sulphate was then left unchanged during the rest of the fermentation.

The effect of the three different pH control regimes (A, B and C) is shown in FIGS. 18, 19, 20 and 21 which show the biomass concentration, total ricin A accumulation, percentage of ricin A partitioning in the soluble fraction and calculated yield of soluble ricin A respectively. FIG. 22 shows the pH of the growth medium during the fermentations. The advantageous effect on yield of soluble ricin of altering the pH for pH6.7 to pH6.0 is clearly illustrated.

EXAMPLE 6

The fermentation process described in Example 4 was repeated, but 11.5 hours post fermenter inoculation the fermentation temperature was decreased gradually.

An unexpected maintenance of ricin solubility was observed. FIGS. 23, 24 and 25 illustrate the results obtained. FIG. 25 shows the fermentation temperature profile during the process.

PREPARATION OF PLASMIDS

The following illustrates the preparation of plasmid pICI 1187 used above. Several intermediate stages in the derivation of the vector used to prepare recombinant ricin A are described.

EXPERIMENTAL PROCEDURES

1. Synthetic oligonucleotides

Synthetic oligonucleotides were used to introduce specific DNA sequence alterations of the ricin gene. All oligonucleotides subsequently described were prepared on an Applied Biosystems 380A DNA synthesiser from 5'-dimethoxytrityl base-protected nucleoside-2-cyanoethyl-N,N-diisopropylphosphoramidites and protected nucleosides linked to controlled-pore glass supports on a 0.2 micro mol scale, according to protocols supplied by Applied Biosystems Inc.

Each oligonucleotide, after cleavage from the solid support and removal of all protecting groups, was dissolved in water (1 ml) and a measurement of absorbance at 260 nm used to determine concentration.

2. Enzymes

A variety of restriction endonucleases and DNA modifying enzymes were used in the manipulations described below. These were purchased from one of a number of suppliers (Amersham International, Bethesda Research Laboratories, Boehringer Mannheim or New England Biolabs) and used in accordance with the manufacturers instructions with respect to reaction conditions.

3. Geneclean (TM)

The kit contains 1) 6M sodium iodide 2) a concentrated solution of sodium chloride, Tris and EDTA for making a sodium chloride/water ethanol/water wash; 3) Glassmilk (TM)—a 1.5 ml vial containing 1.25 ml of a suspension of silica matrix in water.

This is a technique for DNA purification based on the method of Vogelstein and Gillespie published in Proceedings of the National Academy of Sciences USA (1979) Vol 76, p 615.

Alternatively any of the methods described in "Molecular Cloning—a laboratory manual" Second Edition, Sambrook, Fritsch and Maniatis (Cold Spring Harbor Laboratory, 1989) can be used.

4. Sequenase (TM)

Chemically modified T7 DNA polymerase

Based on the procedure of Tabor and Richardson published in "Proceedings of the National Academy of Sciences USA (1987) vol 84 pp 4767–4771.

5. Construction of the pICI expression vectors 5.a) pICI 0020

Plasmid vector pICI 0020 is a pAT153 based plasmid in which the 651 bp EcoRI-AccI region is replaced by a 167 bp EcoRI-ClaI fragment consisting of:

(1) a synthetic *E. coli* trp promoter and trp leader ribosome binding site (2) a translation initiation codon (3) a multiple restriction enzyme recognition sequence derived from M13mp18, containing sites for KpnI, BamHI, XbaI, SalI, PstI, SphI and HindIII (4) a synthetic transcription termination sequence The DNA sequence of this region is shown in FIG. 11.

The construction of a plasmid vector containing a synthetic trp promoter sequence is published (Windass et al Nuc.Acids Res. 10 p6639–6657, 1982). A promoter fragment was isolated from such a vector after digestion with the enzymes EcoRI and HpaI and purification of the appropriate band from an agarose gel by electro-elution (in "Molecular Cloning—A Laboratory Manual", Maniatis, Fritsch and Sambrook, published by CSH laboratory, second edition 1989 and hereinafter referred to as "Maniatis").

A pair of complementary synthetic oligonucleotides were prepared which would ligate to the HpaI end of the promoter fragment providing the natural trp leader ribosome binding site, a translation initiation codon and a 3' KpnI cloning site. These oligonuleotides were mixed in equimolar concentrations and allowed to anneal by heating to 100° C. followed by slowly cooling to room temperature.

The promoter fragment and annealed oligonucleotides were then ligated and the appropriate band isolated from a polyacrylamide gel by electroelution. This fragment was then ligated with an M13mp18 vector derivative containing the trp attenuator sequence (generated from synthetic oligonucleotides) cloned into the HindIII site and introducing an additional ClaI restriction site 3' to the attenuator. The ligated DNA was transfected into *E. coli* strain JM109 (Yanisch-Perron et al Gene, 33, p103, 1985) made competent by the $CaCl_2$ method (Maniatis, chapter 1p82). After plating out and incubation of the plates, plaques were screened by the method of Benton and Davies (Maniatis, chapter 4p41) using a $^{32}P$ labelled probe generated by nick translation of the EcoRI-HpaI promoter fragment isolated previously. Single stranded DNA was prepared from positively hybridising plaques by a standard method (Maniatis, chapter 4p29) and sequenced using the M13 universal primer and the Sanger dideoxy chain termination method as provided in kit form by a number of suppliers eg. Sequenase (United States Bioscience).

RF DNA was prepared from one isolate in which the promoter/ribosome binding site/attenuator sequence had been confirmed. This DNA was digested with EcoRI and ClaI and the appropriate fragment isolated from a polyacrylamide gel as above. Plasmid pAT153 was digested with the enzymes EcoRI and AccI and ligated with the isolated promoter fragment. Ligated DNA was used to transform competent *E. coli* HB101(Bethesda Research Laboratories) and ampicillin resistant colonies selected.

Plasmid DNA from several clones was prepared and DNA sequence derived from the region between the EcoRI and ClaI sites. One clone confirmed as containing the correct promoter/attenuator region was named pICI 0020.

Figure 1A:
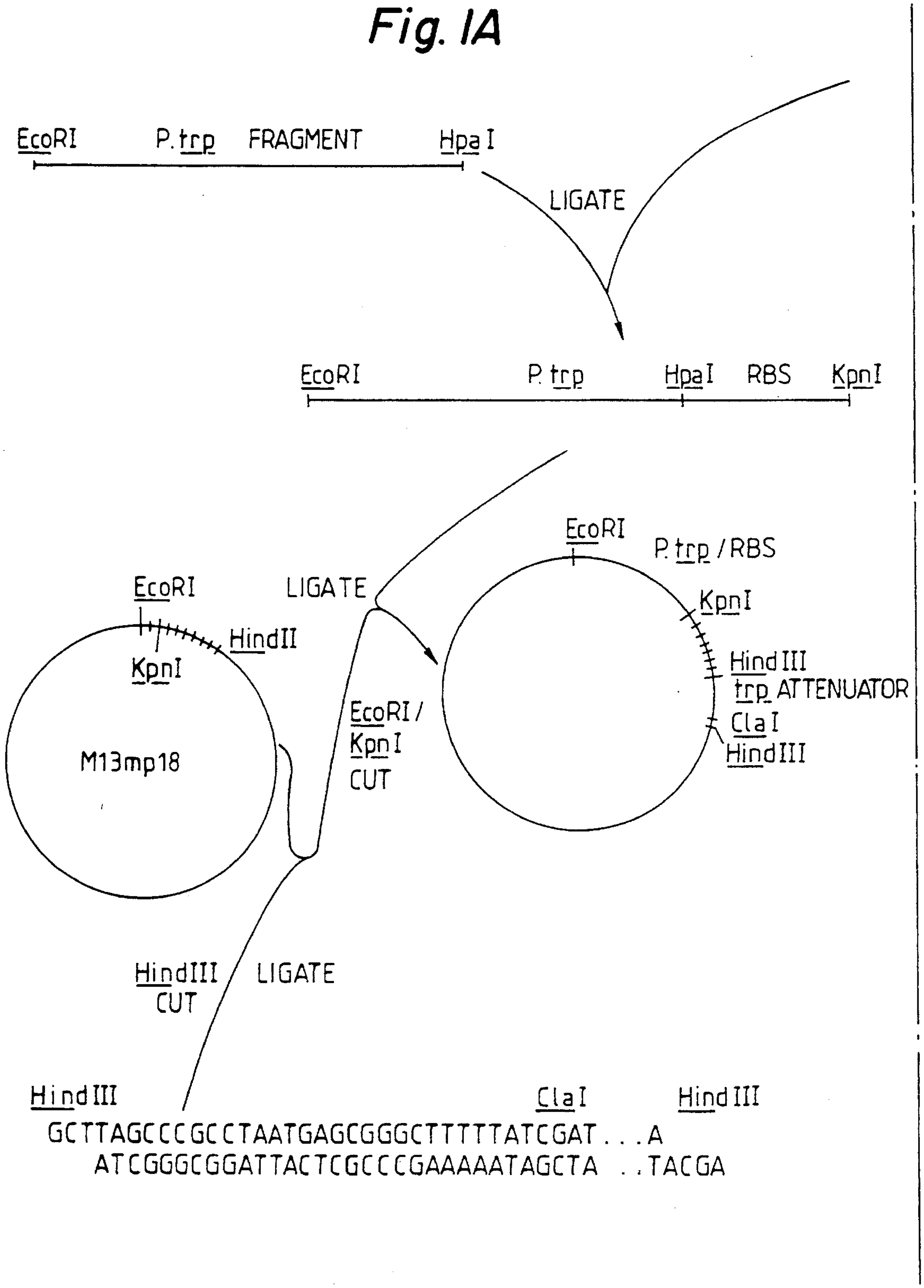
FIG. 1 illustrates the construction of pICI 0020 (SEQ ID NOS:5, 6, 7 and 8)
Figure 1B:
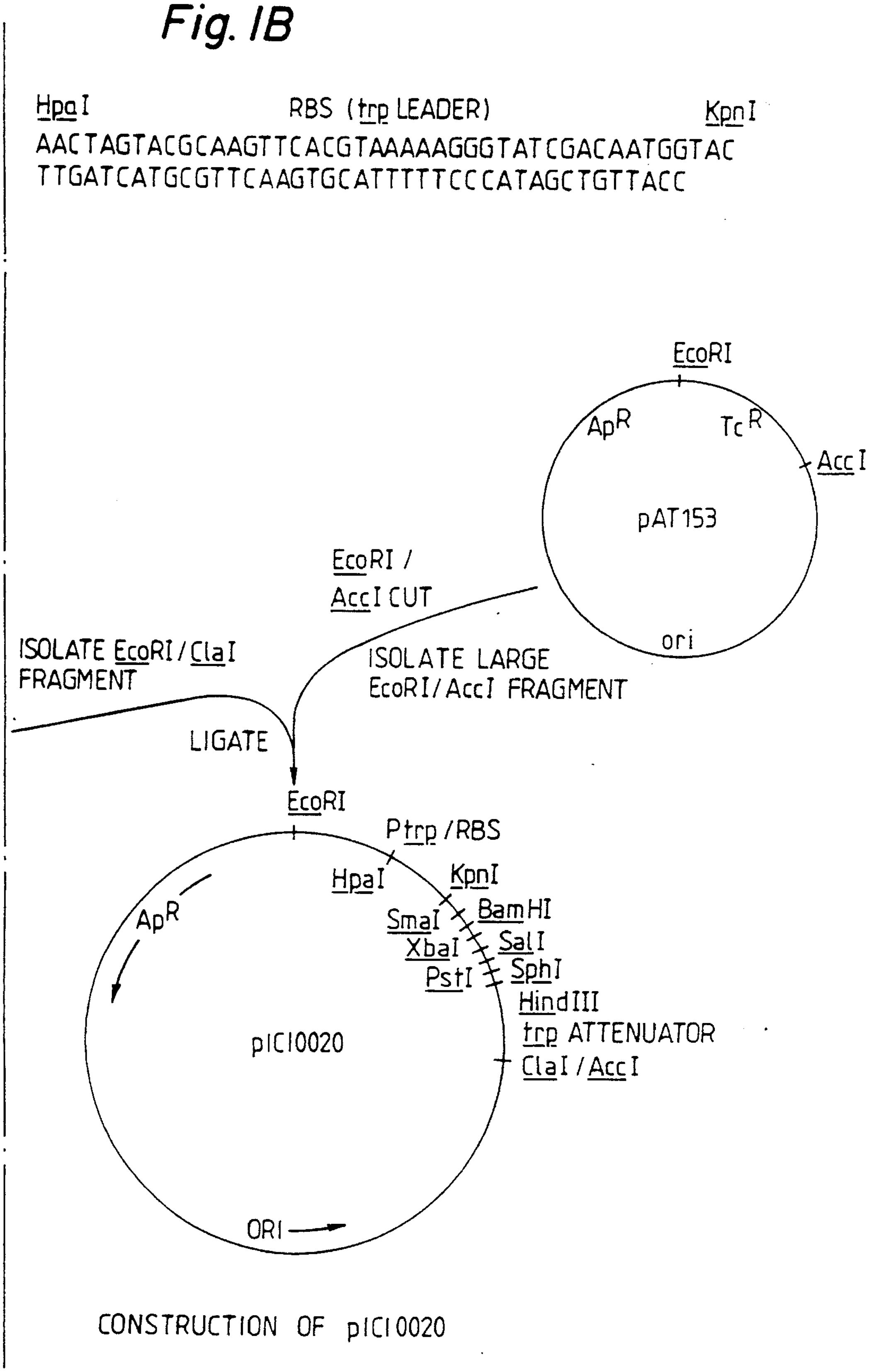

This construction is outlined in FIG. 1.

3.b) pICI 0042 pICI 0042 (FIG. 12) is a plasmid in which the antibiotic resistance markers of pAT153 have been replaced by a single, inducible tetracycline resistance gene from the plasmid RP4 (encoded by the gene tetA and regulated by the product of the tetR gene). These genes have been characterised by Klock et al (J. Bacteriol. 161 p326–332, 1985). A plasmid stability function (cer) has also been incorporated. This obviates the requirement for β-lactam antibiotics in any part of the production process and will also allow assays for these in the final product. Because the new resistance marker is only expressed in the presence of antibiotic, the tetA gene product will not be a potential contaminant of recombinant ricin A in cultures where the plasmid is stabily maintained in the absence of tetracycline.

The initial stage in the generation of this vector was to produce a derivative of pAT153 from which the gene encoding tetracycline resistance had been completely removed. A complementary pair of synthetic oligonucleotides were designed to replace the EcoRI-AvaI fragment from pAT153 with a short sequence containing several unique restriction endonuclease sites for subsequent cloning.

pAT153 plasmid DNA was digested with the enzymes EcoRI and AvaI and the 2.175Kbp plasmid DNA fragment isolated from a 0.7% agarose gel using Geneclean (Bio 101, California) in accordance with the manufacturers instructions. The 1.425 Kbp fragment containing the tetracycline resistance gene is thus removed.

The oligonucleotides (exp79 and 80) were phosphorylated using T4 polynucleotide kinase and equimolar amounts annealed together. A sample of the annealed oligonucleotides was then ligated with the plasmid fragment from pAT153. Ligated DNA was transformed into *E. coli* HB101 (BRL) and ampicillin resistant colonies selected.

Several colonies were picked for small-scale plasmid DNA preparation (method of Birnboim and Doly as specified in Maniatis, chapter 1p25) and the desired construction identified by restriction analysis with suitable enzymes eg. EcoRI, AvaI and BamHI. The structure of 3 isolates identified as having the correct restriction pattern was confirmed by DNA sequence analysis using a pBR322 EcoRI site clockwise primer (New England Biolabs). One isolate was named pICI 0019.

RP4 plasmid DNA was isolated from extant stocks by the method of Holmes and Quigley (Maniatis, chapter 1p29). This DNA was cut to completion with BglII and then partially with XmaI (at 25° C. for up to 35 min) taking samples at various timepoints until a 2.45 Kbp fragment containing the tetR and tetA was clearly identifiable. A sample of pUC8 DNA (Amersham International) was digested to completion with BamHI and XmaI. Ligations were performed to insert the tetracycline resistance genes into the pUC8. Ligated DNA was used to transform *E. coli* C600 (Appleyard, R. K. Genetics 39 p440, 1954) made competent by the $CaCl_2$ method (Maniatis, chapter 1p82) and tetracycline resistant colonies selected. Plasmid DNA was prepared from 8 clones (Holmes and Quigley) and the presence of the RP4 tetR and A genes confirmed by restriction analysis. One of these isolates was named pTB344.

The tetracycline resistance genes were then inserted into pICI 0019 (described above) by replacement of an EcoRI/PstI fragment from pICI 0019 with the corresponding fragment from pTB344. This results in replacement of the majority of the ampicillin resistance gene in pICI 0019 with the tetracycline resistance genes. After digestion and ligation of the plasmid DNAs, followed by transformation of *E. coli* C600, colonies were selected on the basis of phenotype ie. $Tc^R$ and $Ap^S$. Plasmid DNA was prepared from 4 such clones and digested with a combination of enzymes eg. BamHI/PstI/SstI, EcoRI/SalI, SmaI, StyI/SalI and AvaI/PstI. All 4 clones produced restriction patterns consistent with the desired construct. One of these was designated pTB351.

Summers and Sherratt (Cell 36 p1097–1103, 1984) have shown that the instability of plasmids derived from ColEI (eg. pAT153) is due to the loss of a 283bp sequence, cer, present in the parent plasmid. This sequence helps prevent the formation of plasmid oligomers, the latter appearing to disrupt plasmid partitioning in some as yet undefined way. The cer sequence (Summers, D. et al MGG 201, p334–338, 1985) was kindly provided by Prof. D. Sherratt in the form of a fragment cloned into pUC18 (pKS492). pKS492 plasmid DNA was digested with BamHI and TaqI to release a 289bp cer-containing fragment. Plasmid pTB351DNA (isolated from the dam host *E. coli* GM48—Arraj, J. A. and Marinus, M. G. J.Bact. 153 p562–565, 1983) was digested to completion with BamHI and ClaI and ligated with the digested pKS492 DNA. After transformation of competent *E. coli* C600 with ligated DNA, tetracycline resistant colonies were selected. Restriction analysis of plasmid DNA from putative clones with the enzymes AvaI, MluI and PvuI was used to confirm the presence of cer. One isolate with the correct structure was named pICI 0042.

Figure 2:
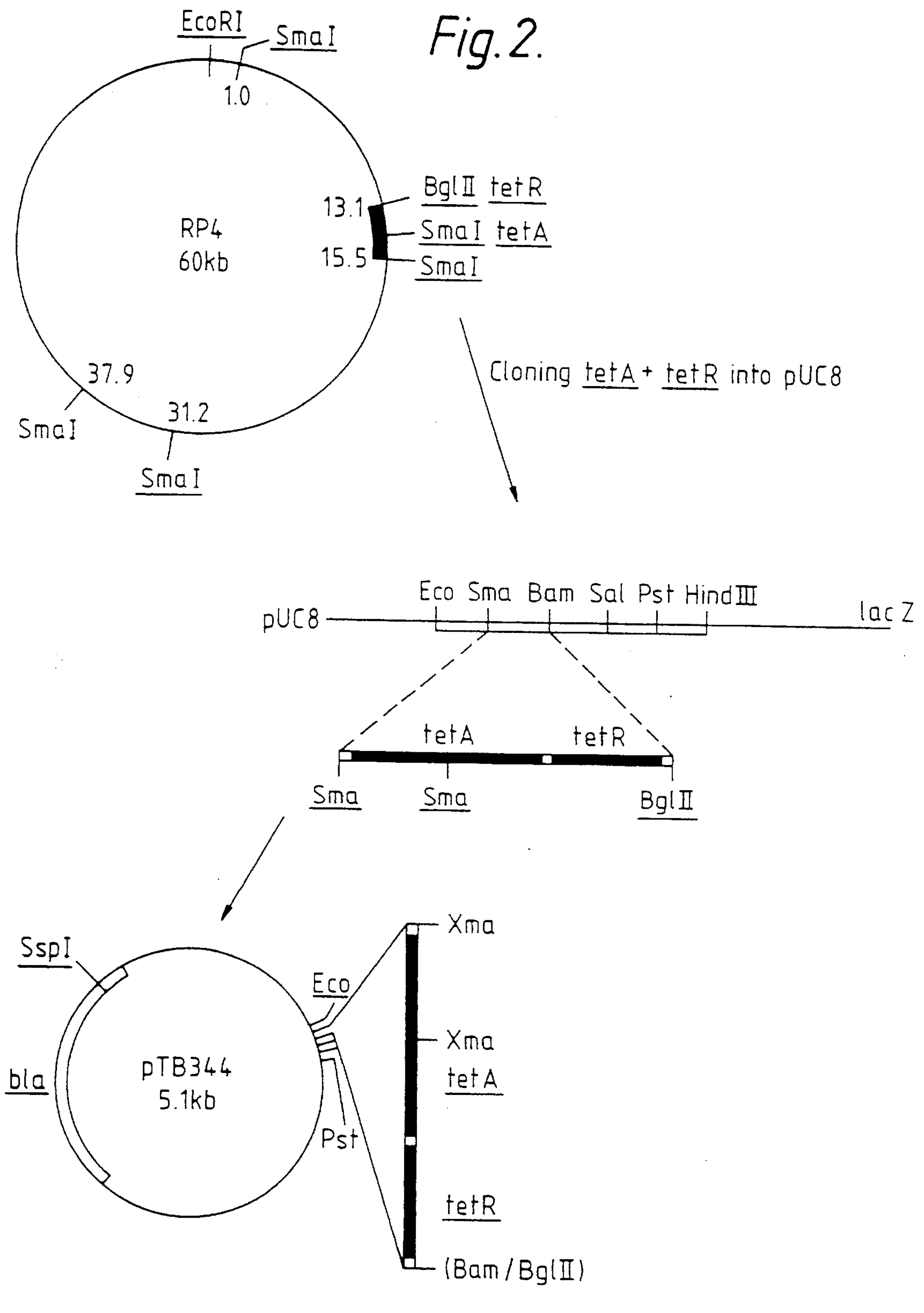
FIG. 2 illustrates the construction of pTB344.
Figure 3A:
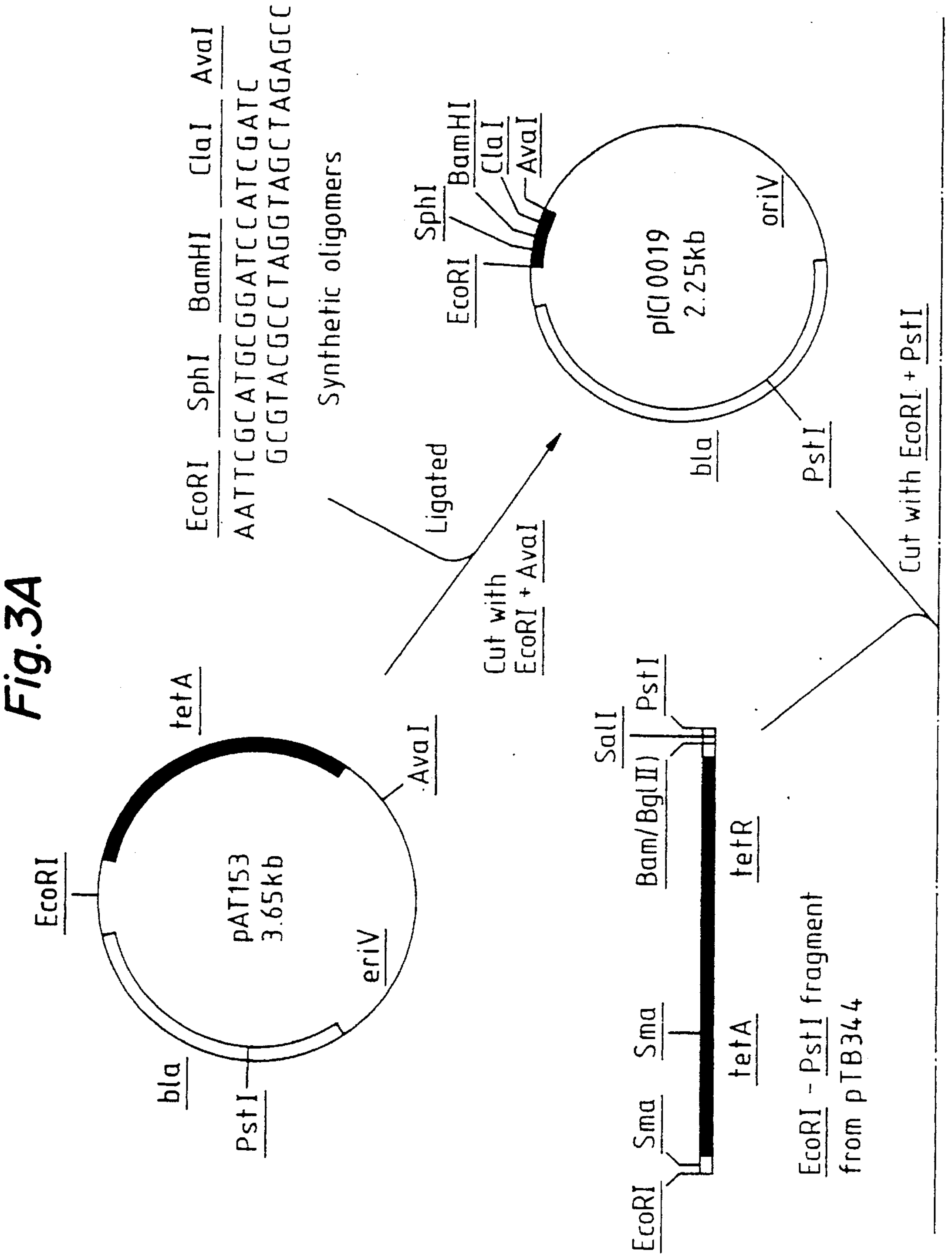
FIG. 3 illustrates the construction of pICI 0042 (SEQ ID NOS:9 and 10)
Figure 3B:
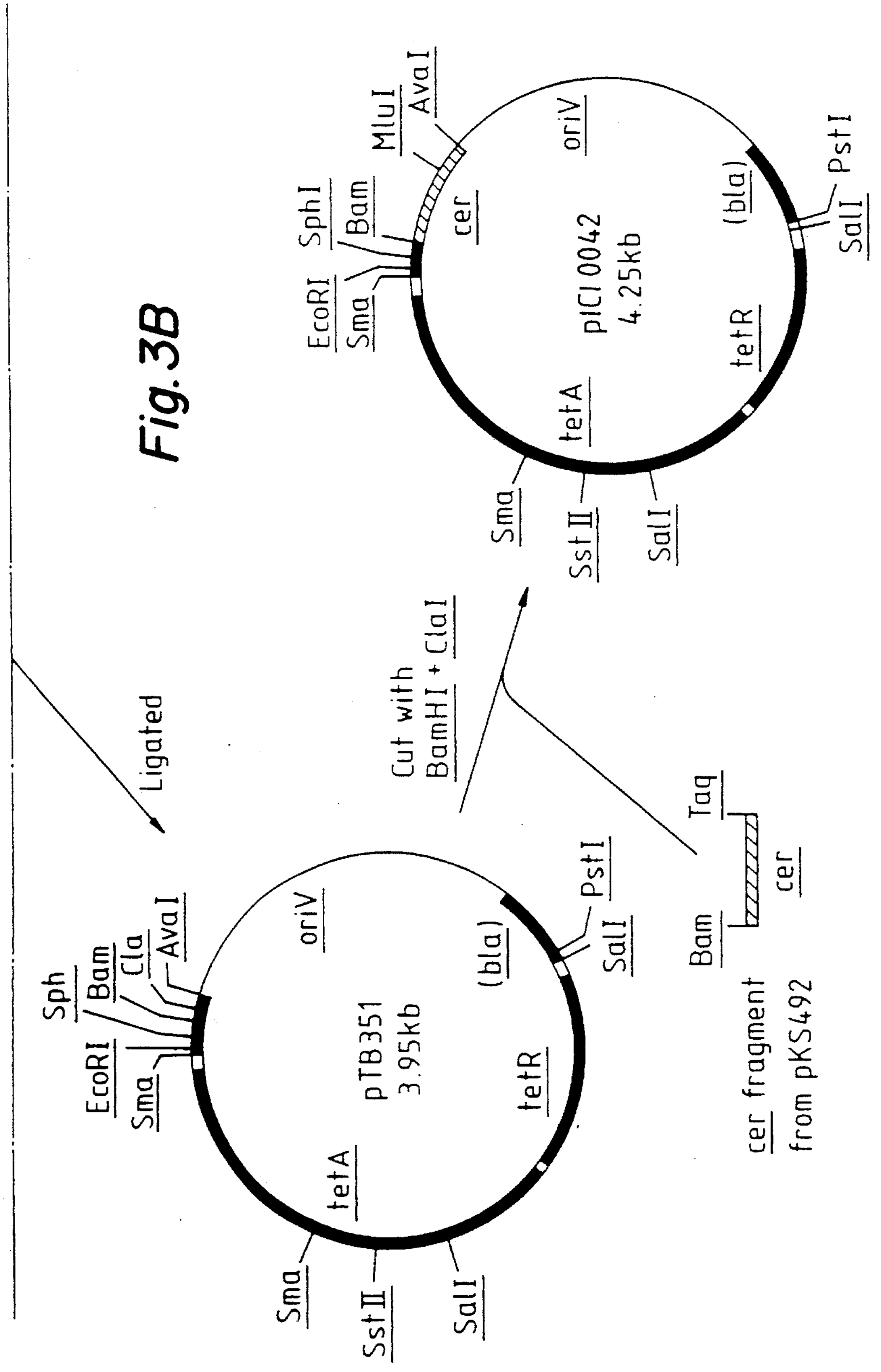

The construction of these plasmids is outlined in FIGS. 2 and 3.

5.c) pICI 1079

Plasmid vector pICI 1079 is an ampicillin resistant, pAT153-derived plasmid containing the following elements between the EcoRI and StyI restriction sites:

(i) a CI857 gene from phage λ;

(ii) a $\lambda P_L$ promoter;

(iii) a synthetic ribosome binding site;

(iv) a synthetic interferon λ2 gene sequence;

(v) a synthetic transcription terminator sequence, derived from phage T4, between the SalI and StyI restriction sites. The DNA sequence of this transcription terminator is shown in FIG. 13. pICI 1079 is illustrated in FIG. 14. pICI 1079 has been deposited under the Budapest Treaty. The deposit has been made at the NCIMB, 23 St Machaer Drive, Aberdeen, Scotland.

This plasmid was used to provide a source of the T4 transcription terminator for the generation of the ricin A expressing clone pICI 1185 (see 7.d below). The starting point for the generation of this plasmid was pICI 1043. pICI 1043 is a plasmid based on pICI 0020 (see 3.a above) in which an expression cassette containing a $\lambda P_L$ promoter and interferon α2 gene (Edge et al Nuc.Acids Res. 11 p6419–6435, 1983) is present between the EcoRI and SalI sites.

A complementary pair of oligonucleotides was synthesised to generate the transcription terminator from gene 32 of bacteriophage T4 with 5' SalI and 3'SphI cohesive ends. This fragment was ligated with a plasmid fragment isolated from pICI 1043 which had been digested to completion with SalI and SphI. The intermediate plasmid thus produced (pICI 1078) contained both the T4 terminator and trp attenuator sequences in tandem.

A second pair of complementary oligonucleotides was then used to replace the trp attenuator sequence (and remaining part of the tetracycline resistance gene) by insertion between the SphI and StyI sites of pICI 1078. A unique BamHI site was introduced within this synthetic fragment.

Figure 4:
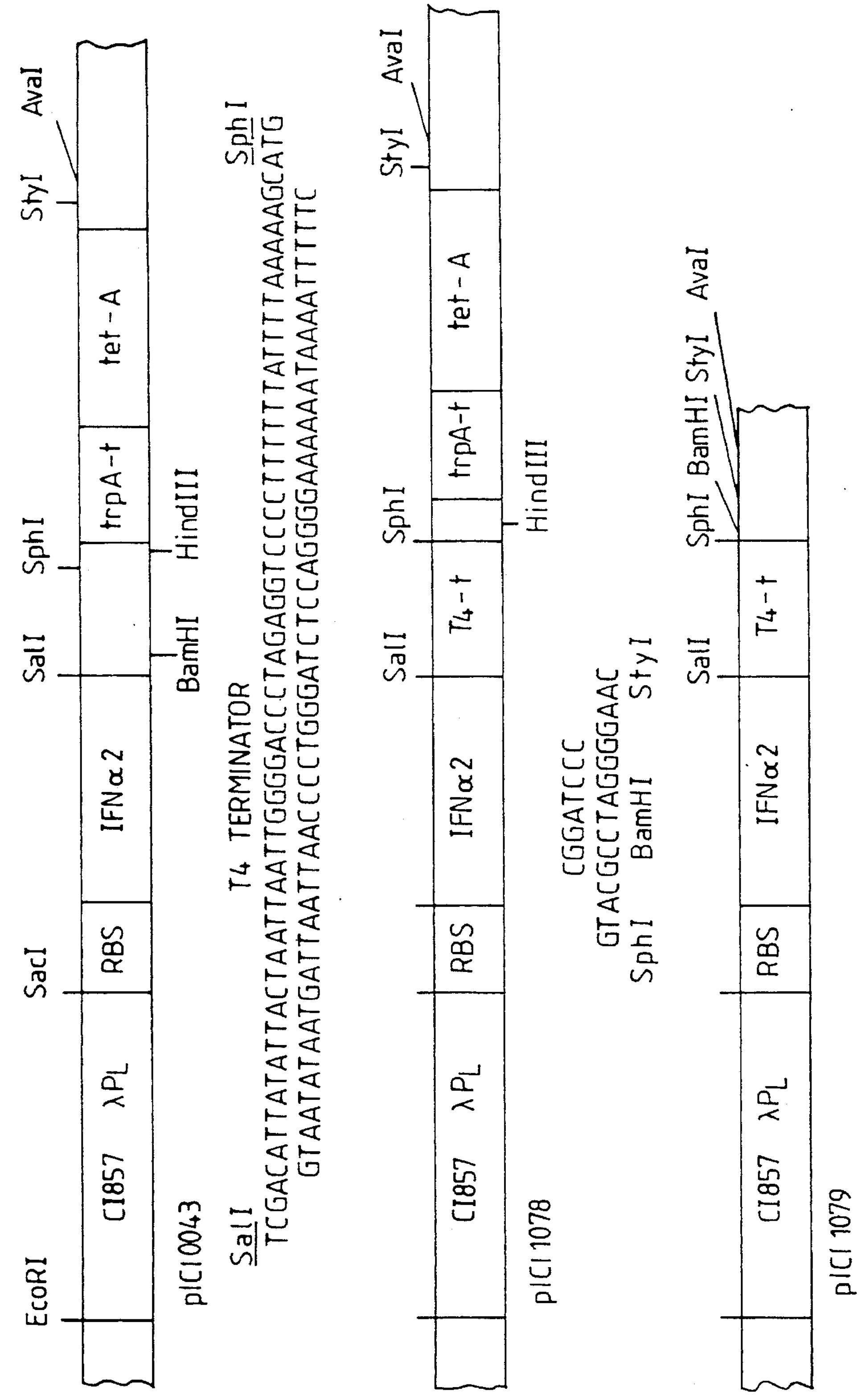
FIG. 4 illustrates the construction of pICI 1079 (SEQ ID NOS:11, 12, 13 and 14)

These manipulations are outlined in FIG. 4.

6. Generation of a ricin A expressing clone 6.a) Preparation of pUC8RA plasmid DNA A clone (pUC8RA) was generated which contains the cDNA for ricin A. This clone contains A-chain cDNA from base number −74 in the leader sequence through to the BamHI site within the B-chain (base number 857) according to the published cDNA sequence (Lamb, I. F., Roberts, L. M., Lord, J. M. Eur.J.Biochem, 1985, 148, p265–270) in plasmid pUC8 (Vieira, J and Messing, J. Gene, 19, p259, 1982). In addition, site-directed mutagenesis has been used to generate a translation termination codon immediately 3' to the final codon of mature ricin A (as reported in O'Hare, Met al FEBS Letts, 1987, 216, p73–78). The entire A-chain coding region is included in a BamHI fragment from this clone.

A small quantity of pUC8RA plasmid DNA was obtained from the originators. For future stocks, a dilution of this DNA was used to transform *E. coli* DH5α competent cells (Bethesda Research Laboratories) and an ampicillin resistant transformant selected. Plasmid DNA from this clone was prepared by a modified Birnboim-Doly procedure (Maniatis, chapter 1p25). Samples of this DNA were digested with BamHI and BanI separately and compared to corresponding digests of the original sample of DNA after electrophoresis on an agarose gel. No differences in restriction pattern were observed and, on this basis, the two DNA samples were assumed to be identical.

6.b) Sub-cloning into M13

BamHI digests of pUC8RA plasmid DNA and RF (replicative form) DNA from the phage M13 strain K19 (Anglian Biotechnology) were "shotgun" ligated using standard conditions (Maniatis, chapter 1p68). Control ligations were also performed. The ligated DNAs were used to transform *E. coli* strain TG1 (Gibson, 1984/Anglian) made competent by the $CaCl_2$ method (Maniatis, chapter 1p82).

The transformation frequences indicated efficient ligation and recombinant phage were expected in the progeny. Recombinant phage were predicted to produce clear plaques on IPTG+X-gal (BRL) containing plates due to disruption of the lacZ (β-galactosidase) gene. Wild type phage produce blue plaques due to conversion of the X-gal by β-galactosidase.

Several clear plaques were picked for single strand DNA preparation. Direct gel electrophoresis of lysed phage suspensions indicated that one phage clone contained a sizeable insert which was confirmed by sequencing to be the ricin A-chain coding sequence. Only 182 bases of the mature ricin A coding sequence were confirmed but this was taken as sufficient evidence for the presence of the entire ricin A gene. This clone was named M13K19RA 6.c) Mutagenesis of M13K19RA To generate a KpnI site, compatible with pICI expression vectors, at the start of mature ricin A, the following changes (underlined) are necessary:

SEQ.ID NO: 1

5' . . . GATAACAACATATTCCCCAAA . . . 3'

. . . Ricin leader sequence . . . | —Mature ricin A —>

Changed to:

5' . . . GATAACAACATGGTACCCAAA . . . 3' SEQ.ID NO: 2

| KpnI

|

Translation initiation and result in an ATG codon overlapping a KpnI site. A KpnI fragment containing ricin A can be excised from the mutant and inserted into the ICI expression vector series. Two N-terminal amino acid modifications are made (ile-phe to met-val).

The single stranded DNA prepared from M13K19RA was the template for the mutagenesis step for each mutation strategy. A single oligonucleotide (DTR16) introducing all the mutational changes for this strategy was synthesised.

SEQ.ID NO: 3

DTR16 5' AACAACATGGTACCCAAACAA 3'

Several protocols exist for the introduction of specific DNA sequence changes by site directed mutagenesis. The procedures outlined below were achieved using the method of Eckstein et al (Nuc. Acid Res., 1985, 13 p8749–8764 and 1986, 14, p9679–9698) as provided in kit form (Amersham International) and used in accordance with the manufacturers instructions.

The principle of this method is to prime the single-stranded DNA template with the mutagenic oligonucleotide and synthesise the complementary strand incorporating dATPαS in place of dATP. Using this nucleotide results in the formation of phosphorothioate bonds which are not cleaved by certain restriction enzymes (eg. NciI). After synthesis of the second strand, NciI is used to nick the parent strand and exonuclease III added to digest back past the mutation point. DNA polymerase I then allows resynthesis of the parent strand. Consequently, the mutagenic oligonucleotide acts as a template for resynthesis and the mutation is introduced into both strands prior to transformation. Mutation frequencies up to 96% of the total progeny are claimed and screening is performed simply by picking plaques at random for DNA sequence analysis.

In our experiments 4 out of 4 plaques picked were correctly mutated.

Having chosen one mutant (MRA16), RF DNA was prepared and checked for the presence of the newly generated restriction fragment ie KpnI.

6.d) Cloning, Expression and Initial Characterisation

The pICI series of expression vectors (see section 5) can accept DNA fragments cloned into a unique KpnI restriction site adjacent to the Trp promoter. The KpnI site overlaps the translation initiation codon (ATG) which is situated 8 bp downstream from the Shine-Dalgarno site (AGGA) of the promoter.

Having verified the sequence of MRA16, a large scale (~5 μg RF DNA) KpnI digest was performed and the relevant ricin A coding DNA fragment isolated from an agarose gel (Nu-Sieve GTG agarose, FMC Bio-products) by phenol extraction of an excised gel slice according to the manufacturer's protocol.

pICI 0020 (see 5a) was digested with KpnI and then dephosphorylated using calf intestinal alkaline phosphatase (CIP—Boehringer Mannheim). The latter treatment prevents recircularisation of the vector upon ligation which would lead to a high proportion of parentals in the transformation progeny.

Ligations were set up with ratios of plasmid vector to isolated fragment from 8:1 (w/w) to 1:3 for the various strategies. Control ligations to test the effectiveness of phosphatase treatment, ligase activity etc., were included. The ligation conditions were appropriate for the source of T4 DNA ligase used (New England Biolabs or Amersham). Reactions were generally incubated at 15° C. overnight.

Fifty percent of each ligation (5 μl) reaction was diluted to 100 μl with 1×TNE (50 mM Tris, 50 mM NaCl, 1 mM EDTA) and 200 μl of competent *E. coli* DS410 added. After a standard transformation protocol (Maniatis, chapter 1p74), the cells were plated onto L agar plus streptomycin (25 μg/ml) and ampicillin (100 μg/ml) and incubated at 37° C. overnight. *E. coli* DS410 has a chromosomal streptomycin resistance gene.

The transformation plates were examined after incubation. In general, 5 to 10 times more colonies were seen in ligations compared to controls without ligase. In some cases, little difference in the number of colonies produced in the presence or absence of ligase occurred indicating incomplete digestion of the vector or poor ligase activity.

Transformants, plus the relevant controls were picked onto nitrocellulose filters placed on L agar plates for hybridisation screening (based on the method of Grunstein and Hogness as described in Maniatis, chapter 1p98). After incubation, the colonies were lysed in situ using 10% SDS and 1M NaOH, neutralised using 1M Tris (pH 7.5) and dried under vacuum at 80° C. for 2 hours.

Hybridisation probes were generated by $^{32}$p labelling of the mutational oligonucleotides using T4 polynucleotide kinase. The filters were probed at room temperature and then washed in stages up to 55°–65° C. to remove non-specifically bound counts before autoradiography. Specific hybridisation indicated putative clones containing ricin A DNA.

Small scale DNA preparations (by the methods of Holmes and Quigley or Birnboim-Doty as specified in Maniatis, chapter 1p25) were made from positively hybridising clones. The DNAs were digested with the relevant restriction enzymes eg. KpnI and EcoRI/BglII, and analysed by electrophoresis on agarose gels. Vector DNAs and mutated RF DNAs were cut with the same enzymes to demonstrate the fragment sizes expected for the correct clones.

Larger scale plasmid DNA preparations (Birnboim-Doty) of each clone were used for more detailed restriction analysis, eg. ClaI, HindIII, BamHI, EcoRI/BglII, KpnI, and ScaI. On agarose gels, these digests showed the size of fragment inserted, an indication of its orientation and the gain of some unique ricin A-chain enzyme sites.

6.e) Expression studies

The clones positively identified by hybridisation and restriction screening were tested for expression of ricin A by SDS-PAGE analysis of total cell lysates. The standard conditions for expression studies were:

1) Inoculate 10 ml of L-broth+antibiotic(s) with a single colony and grow at 37° C. overnight with gentle shaking.

2) Take 750 μl of the L-broth overnight and pellet the cells in a microfuge (1 min at 6500 rpm).

3) Resuspend pellet in 300 μl M9 medium (Maniatis, appendix A.3)+0.02% casein hydrolysate +0.2% glucose+50 μg/ml thiamine and inoculate into 10 ml of same.

4) Incubate for 7 hours or overnight at 37° C. with gentle shaking.

5) After incubation, measure $OD_{540}$, pellet the cells and resuspend to $OD_{540}$=10 per ml in Laemmli sample buffer (Maniatis, chapter 18p53). Boil for 15 minutes.

6) Load 20 μl of total cell lysate on an SDS polyacrylamide gel, electrophorese, stain with Coomassie blue, destain and visualise.

Of the clones studied by SDS-PAGE, only 1 showed an additional band with equivalent molecular weight of ~29 KD (equivalent to that estimated for unglycosylated, mature ricin A). Gel scans indicated the expression level to be in the range of 5–10% of total cell protein. This clone was named pICI 1102.

Figure 5:
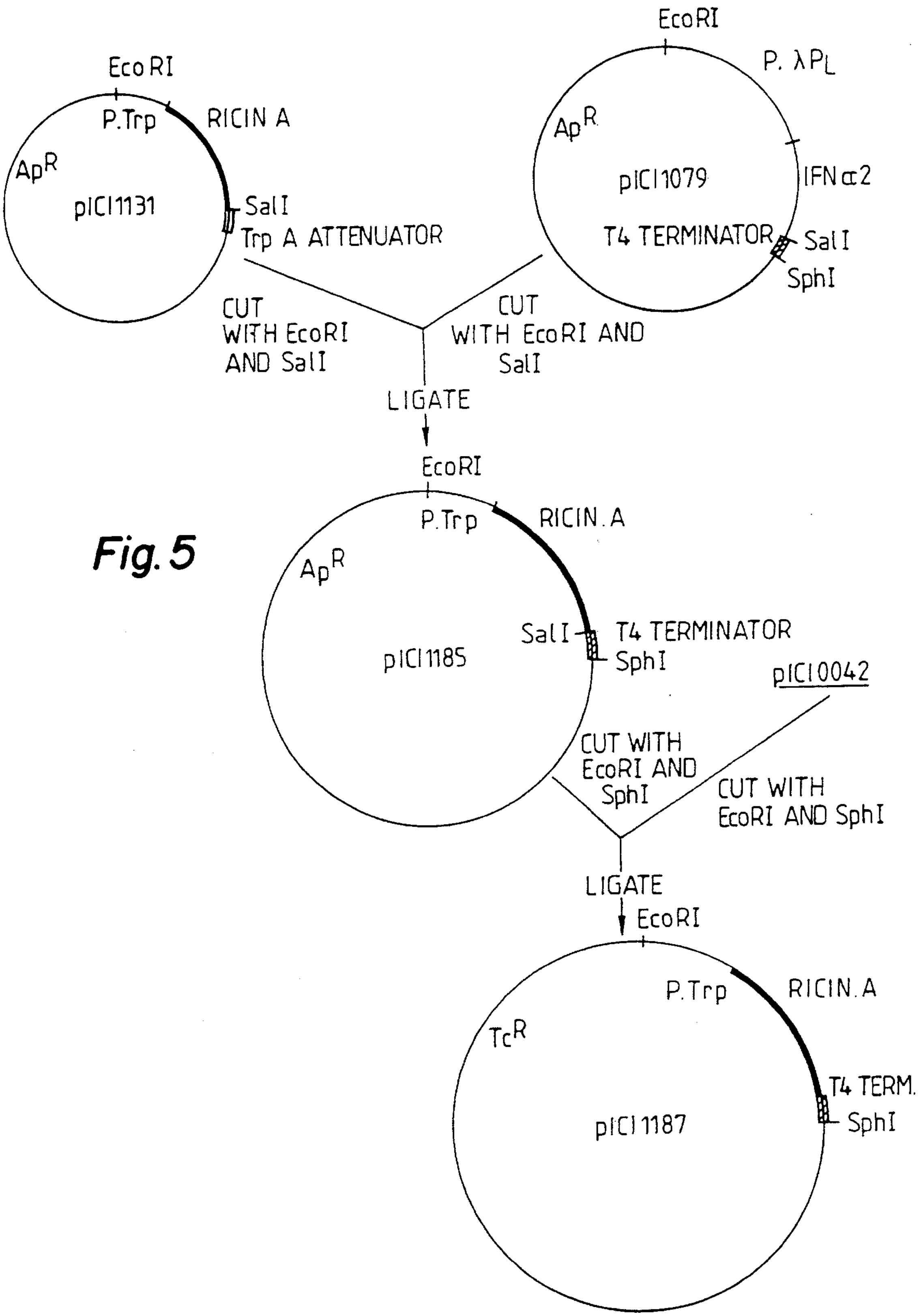
FIG. 5 illustrates the construction of pICI 1187.
Figure 6:
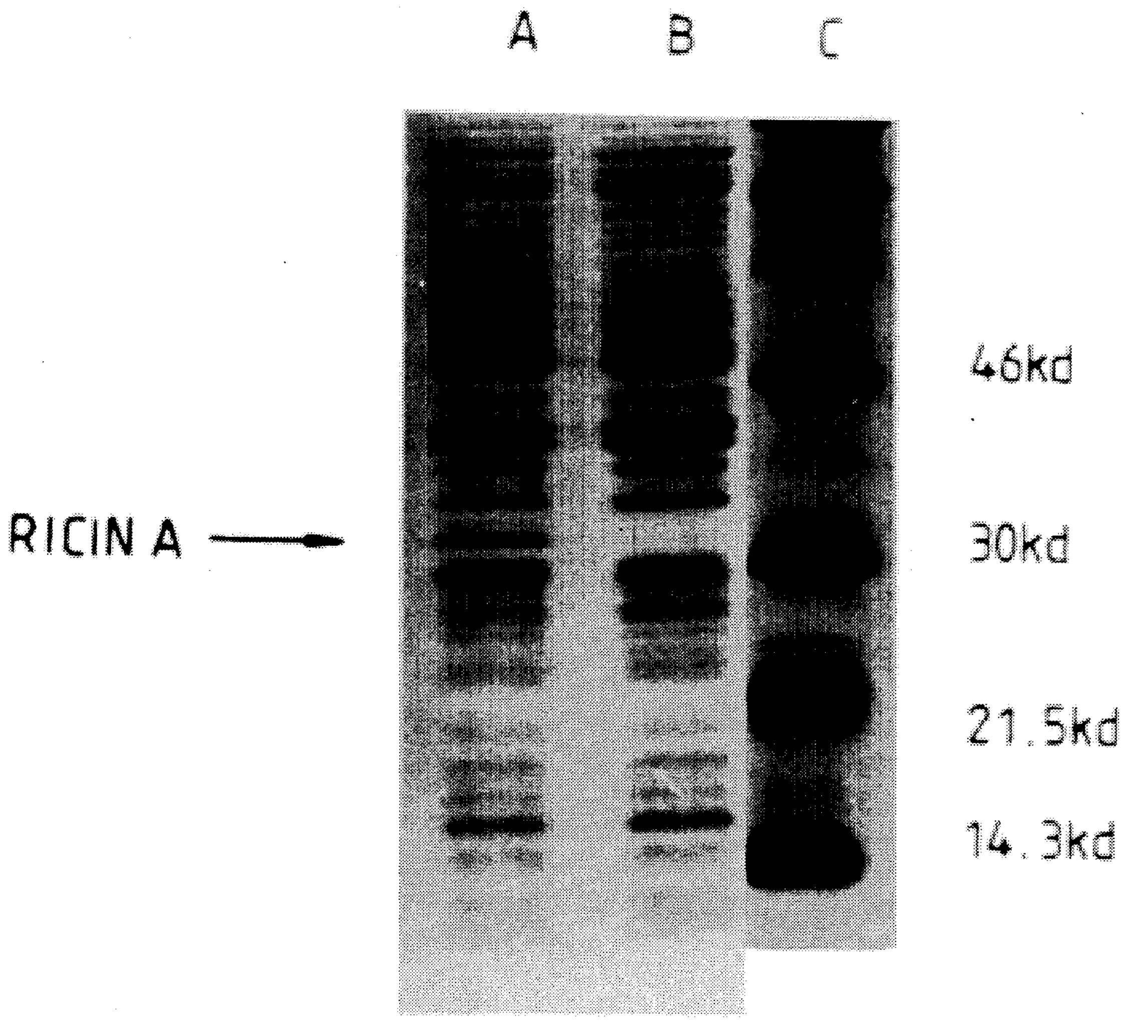
FIG. 6 illustrates a Coomassie blue-stained SDS gel of *E. coli* lysates in which track A is pICI 1102; B is pICI 0020, and C is molecular weight markers.
Figure 7:
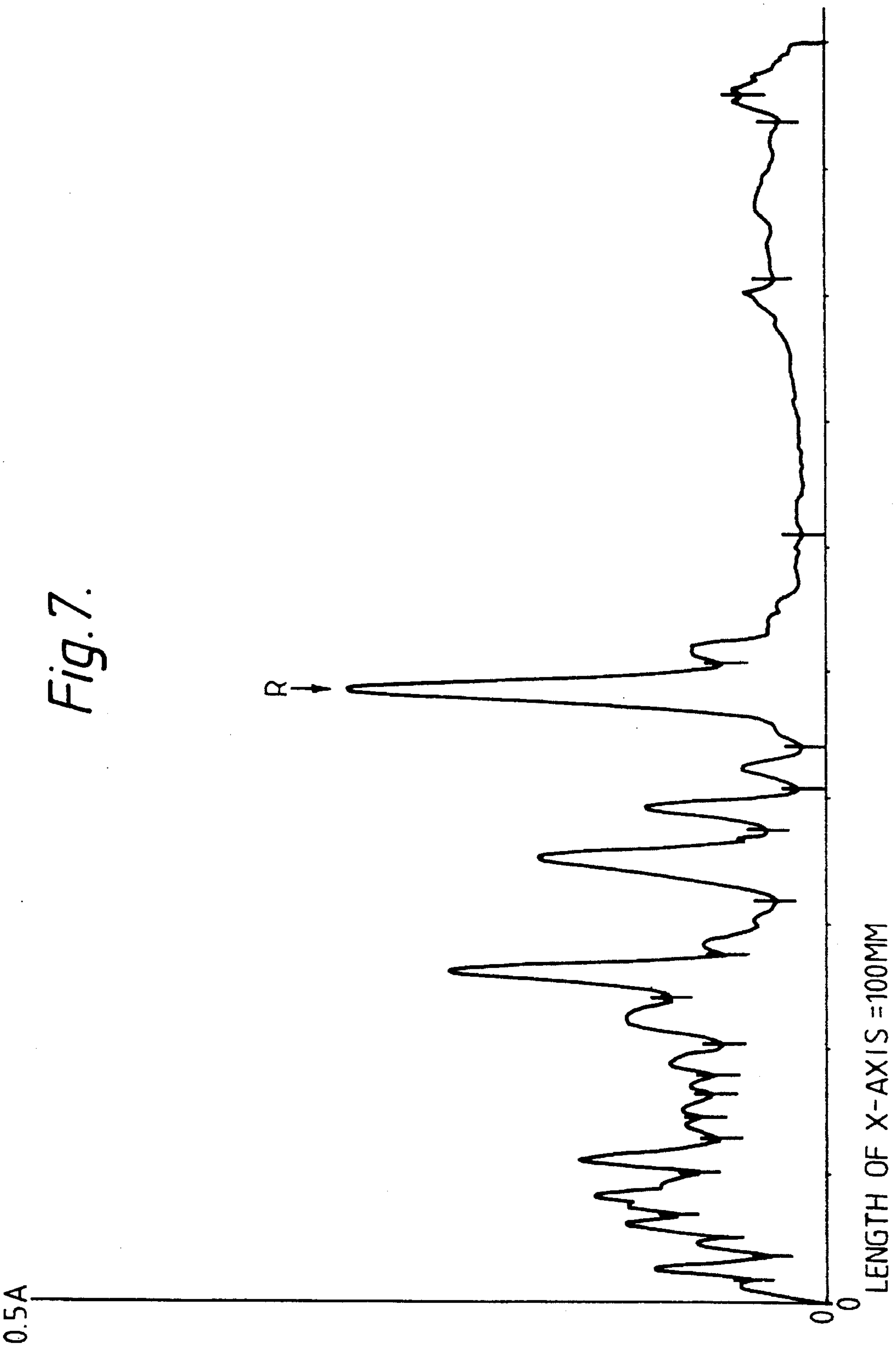
FIG. 7 illustrates a gel profile of pICI 1102 in which peak R represents ricin A.

The construction of pICI 1102 is outlined in FIG. 5. Results of expression studies are shown in FIGS. 6 and 7.

6.f) Western transfers and immunodetection of recombinant ricin A

Authenticity of recombinant ricin A-chain protein, initially observed by Coomassie blue staining of SDS-polyacrylamide gels, was confirmed by Western blotting. The protein bands were transferred to nitrocellulose filters and detected using a ricin A specific antibody followed by peroxidase labelled antiglobulins.

15% SDS-PAGE gels were run overnight at 8 mA then equilibrated for at least 30 minutes in transfer buffer.

Protein bands on the gels were then transferred to nitrocellulose membranes (Hybond-C, Amersham) electrophoretically in a Bio-Rad Trans Blot apparatus at 70 V for 3 hours. The filters could be stored, after drying, in sealed plastic bags at −20° C.

Ricin A.1 was a polyclonal antibody raised in rabbits against a synthetic peptide fragment of ricin A. Preliminary studies showed good affinity for ricin A but considerable cross-reactivity with many *E. coli* proteins. To overcome the high background caused by this cross-reactivity the antibody was pre-incubated with an *E. coli* lysate.

Thus, a 10 ml L-broth overnight culture of *E. coli* strain DS410 was centrifuged at 4000 rpm for 10 minutes to pellet the cells. The pellet was resuspended in 5 ml of bacterial buffer and sonicated at 4–6μ for 6×10 second bursts with 30 seconds cooling intervals on ice.

0.5 ml of sonicate was then mixed with 0.5 ml of ricin A.1 antiserum and incubated at room temperature for 90 minutes. Cell debris was spun down at 13000 rpm for 5 minutes and the supernate stored at −20° C.

The nitrocellulose filters from Western transfers were blocked by incubation overnight at room temperature in 5% BSA-PBS/Tween. (PBS Tween =5 ml Tween 20 per 1 liter of PBS).

Washed 3×3 minutes in PBS/Tween.

Incubated 2 hours (or overnight) at room temperature with a 1/4000 dilution of "blocked" Ricin A.1 antibody in 0.5% BSA-PBS/Tween.

Washed 3×3 minutes in PBS/Tween.

Incubated 1 hour with a 1/1000 dilution of goat anti rabbit antiserum in 0.5% BSA-PBS/Tween at room temperature.

Washed 3×3 minutes in PBS/Tween.

Incubated 1 hour with a 1/5000 dilution of rabbit peroxidase anti-peroxidase antiserum in 0.5% BSA/PBS/Tween at room temperature.

Washed 3×3 minutes in PBS/Tween.

Developed by immersion in a solution of 4-chloronaphthol (60 mg) in 20 ml methanol made to 120 ml with PBS and containing 12 μl hydrogen peroxide. The membrane was removed from the solution as soon as bands were visible, dried and photographed.

A typical Western blot analysis is shown in FIG. 8.

6.g) Biological assay for recombinant ricin A protein

The aim here was to establish conditions under which samples generated during the ricin A-chain purification from *E. coli* cells could be tested for biological activity in a cell-free in vitro protein synthesis assay.

Rabbit reticulocyte lysates were prepared according to the method of Allen and Schweet (J Biol Chem (1962), 237, 760–767). The assay demonstrates inhibition of protein synthesis in a cell-free system by a lack of incorporation of $^{14}C$-labelled leucine into newly synthesised protein.

6.g.i) The assay protocol

Stock solution: 1 mM amino acid mix minus leucine.

A solution containing all L-amino acids at 1 mM except leucine (adjusted to pH7.4 with NaOH and stored at −70° C.).

Soln. A 40 mM Magnesium acetate

2M Ammonium acetate 0.2M Tris (pH 7.4 with HCl, stored 4° C.)

Soln. B

ATP (Sigma A5394) 246 mg/ml

GTP (Sigma G8752) 24.4 mg/ml

Assay mix:

1 ml Amino acid mixture 1 ml Soln. A 0.1 ml Soln. B 103 mg Creatine phosphate 1 mg Creatine kinase 510 μl $H_2O$ 600 μl (60 μCi) L-$^{14}C$-leucine (New England Nuclear, NEC-279E)

Reaction mix:

Test sample 25 μl

Assay mix 12.5 μl

Rabbit reticulocyte lysate 25 μl

Blank solution was 2 mg/ml BSA in PBS

All assays were done in duplicate 12.5 μl of assay mix placed in sterile glass tubes 25 μl of BSA in PBS added to each of first four tubes for blanks 25 μl of test samples added to rest of tubes 1 ml 0.1M KOH added to first two tubes (background blank) Tubes equilibrated to 28° C. in a water bath 25 μl of rabbit reticulocyte lysate (allowed to thaw from liquid nitrogen temperature) were added to each tube at 20 second intervals.

When first tube had incubated for 12 minutes, 1 ml 0.1M KOH was added to each tube again at 20 second intervals to allow all tubes to have 12 minutes incubation. Two drops of 20% hydrogen peroxide were added to each tube followed by 1 ml of 20% TCA.

Tubes were mixed and allowed to stand for at least 1 hour, or overnight, at 4° C. The precipitates were filtered on to 2.5 cm GFC discs, washed with 3×4 ml of 5% TCA, transferred to scintillation vials and 10 ml scintillant (Ready-Solv. MP, Beckman) added. After 1 hour the vials were shaken and counted.

6.g.ii)Establishment of technique for use with *E. coli* lysates 10 ml L-broth overnight cultures were grown at 37° C. 400 μl aliquots were pelleted at 13000 rpm for 30 seconds and most of the supernate decanted.

The pellets were subjected to 2 rounds of rapid freezing in dry ice/EtOH followed by thawing at 37° C. 12 μl of 25% sucrose in 50 mM Tris HCl pH8.0 were added followed by 4 µl of a 10 mg/ml solution of lysozyme.

After incubation on ice for 15 minutes, 8 µl of 0.25M EDTA were added and incubation continued for 15 minutes. Lysis was brought about osmotically by diluting the samples to 400 µl with water. This procedure produced viable cell counts of 80–100 per ml.

When a 25 µl aliquot of this lysate was added into the assay reaction mix, the level of incorporation of $^{14}$C-leucine into newly synthesised protein was ~10% of the blank without lysate. This was a similar level of inhibition to that produced by 8 ng/ml ricin A. Dilutions of the *E. coli* lysate were then prepared and the assay repeated. The result clearly showed that a minimum 16-fold dilution was necessary to reduce the effect of the lysate to equal that of the blank.

In order to be as confident as possible that lysis of *E. coli* and *E. coli* lysates would not compromise ricin A toxicity, 2 control assays were performed. The first added plant-derived ricin A to a 16X diluted *E. coli* cell pellet so as to give a final concentration of 8 ng/ml in the assay mix after cell lysis. Both these controls showed no deleterious affect from the lysates or the lysis procedure on the inhibitory action of ricin A.

coding region. Also, there is an in-frame termination codon (TAG) prior to the ricin A initiation codon and a putative Shine-Dalgarno sequence (AGGA) which could re-initiate translation from the second ATG.

Subsequent studies revealed that, surprisingly, this additional DNA fragment conferred a beneficial advantage with respect to the accumulation level of ricin A-chain in *E. coli* when compared to clones from which it had been excised.

The complete DNA sequence of the ricin A gene contained in pICI 1102 is given in FIG. 9.

7. Generation of subsequent ricin A expressing clones 7.a) Mutation of Ricin-A clone pICI 1102 to allow subcloning To subclone the two KpnI fragments from the fortuitously generated pICI 1120 in the correct orientation for ricin-A expression would be difficult. Consequently, we planned to alter the internal KpnI recognition site by a single base substitution (A to T). This would prevent KpnI cleavage at this site and allow the subcloning of a single KpnI fragment into the range of trp/RBS vectors. By substituting the adenine of the KpnI recognition site (GGTACC) with thymine (ie GGTTCC) the first residue of ricin-A is unaltered (GTA/GTT=Val). ie:

```
KpnI    53bp fragment KpnI             Ricin-A sequence KpnI
_|___________|__________________|___|
GGTACC      ATGGTACC              TGA  GGTACC

Changed to:
 KpnI     53bp fragment             Ricin-A sequence   KpnI
_|___________|__________________|___|__
GGTACC      ATGGTTCC              TGA  GGTACC
                 |
           not recognized by KpnI
```

These techniques were used to verify the synthesis of biologically active, recombinant ricin A from pICI 1102 and the clones described below.

6.h) DNA sequence analysis

Plasmid DNA sequencing was used to analyse pICI 1102. The protocol chosen was modified from Zagursky et al (Gene Analysis Techniques Vol 2, No 5) and involves alkaline denaturation of double stranded plasmid DNA prior to primer annealing and sequencing by a standard procedure such as that provided in kit form by several suppliers, eg. Sequenase (United States Bioscience). By using an oligonucleotide to prime at the 3' end of β-lactamase and several A-chain internal primers, sequencing both strands of the promoter and ricin A gene was possible.

The initial sequencing data revealed an unexpected result in that an additional KpnI fragment was present between the promoter and ricin A coding sequence, ie:

SEQ.ID NO: 4

KpnI

5' AAAAAGGGTATCGACATGGTACCCGGGGATCCACCTCAGGGTGG

KpnI

TCTTTCACATTAGAGGATAACAACATGGTACCCAAACAATAC 3'

The additional KpnI fragment has come from M13K19RA and contains restriction enzyme sites plus the part of the ricin leader sequence cloned from pUC8RA. The 5' region of the ricin A chain contains the base changes induced during mutagenesis.

Study of this sequence reveals that the first translation initiation codon (ATG) is out of frame with that the ricin A The oligonucleotide synthesised to produce this change has the sequence:

5' ATAACAACATGGTTCCCAAACAATAC 3' where the underlined base represents the mutational change.

We planned to clone the mutated ricin-A fragment into a range of trp expression vectors for comparative expression studies. Cloning into pICI 0020 provides a comparison with pICI 1102 to determine the effects on expression, if any, of the single base substitution.

7.b) Mutagenesis

The template for mutagenesis was MRA16 which is the M13 clone containing the two KpnI fragments present in pICI 1102. After mutagenesis, isolates carrying the desired mutations were identified by random sampling and DNA sequence determination over the region to which the mutagenic oligonucleotide binds specifically.

One mutated template was named MRA22. This was analysed further by DNA sequence determination of the entire ricin-A coding sequence to verify the absence of non-specific mutations.

7.c) Sub-cloning

The mutated, single-stranded DNAs were used to transform competent *E. coli* TG1 cells to produce single plaques. Individual plaques were then picked and replicative form (RF, double-stranded) DNA purified by banding on caesium chloride/ethidium bromide buoyant density gradients. The purified RF DNA was digested to completion with KpnI. Cloning was achieved by "shotgun" ligation of the digested RF DNA with the appropriate KpnI cut and phosphatased expression vector or by specific ligation of the ricin-A fragment after its purification from an agarose gel. Ligated DNA was transformed into *E. coli* TG1 or HB101.

Ricin-A containing clones were identified by hybridisation screening using a $^{32}P$ labelled ricin-A probe produced by random hexanucleotide priming of a KpnI fragment isolated from another ricin A containing clone (pICI 1121). Colonies showing positive hybridisation were screened further by restriction analysis of plasmid DNA using a KpnI single digest and an EcoRI/BglII double digest. KpnI identifies the size of the inserted fragment and EcoRI/BglII determines the orientation of the fragment.

Clones confirmed as having the ricin-A fragment in the correct orientation for expression were subjected to clone selection grows and analysis by SDS-PAGE followed by Coomassie staining and Western blotting of duplicate gels. The level of ricin A accumulation in these clones was equivalent to that detected from pICI 1102.

One isolate was selected and named pICI 1131.

7.d) Use of alternative transcription terminator element.

In these experiments, the trp promoter and ricin-A fragment from pICI 1131 was excised by digestion with the enzymes EcoRI and SalI. The latter enzyme cleaves between the 3' terminus of the ricin-A coding sequence and the trpA transcription terminator. The resulting fragment was excised from an agarose gel (2% NuSieve GTG Agarose, FMC Bioproducts) and purified by phenol and chloroform extractions followed by ethanol precipitation. The purified fragment was ligated with pICI 1079 cut with EcoRI and SalI. This latter plasmid contains the $T_4$ terminator between unique SalI and SphI sites.

Ligated DNA was used to transform competent *E. coli* HB101 (BRL) and hybridisation screening used to detect the presence of ricin-A DNA as in previous experiments. Positively hybridising clones were chosen for plasmid DNA preparation followed by restriction analysis with EcoRI and SalI together to show the presence of an appropriately sized fragment.

One isolate with the correct construction was identified and named pICI 1185.

7.e) The use of alternative plasmid background.

Plasmid DNA was prepared from pICI 1185 and digested with EcoRI and SphI together to excise an expression cassette containing the trp promoter/RBS1/ricin-A (MRA22) fragment/$T_4$ terminator. This fragment was isolated by the method outlined in 6.d and ligated with pICI 0042 cut with EcoRI and SphI.

Ligated DNA was used to transform *E. coli* HB101. HB101 transformations were plated on L agar+tetracycline, incubated at 37° C. overnight, and colonies screened by hybridisation with a $^{32}P$ labelled ricin-A DNA probe.

In both cases, positively identified colonies were confirmed by restriction analysis of plasmid DNA using EcoRI/SphI and EcoRI/BglII digests. Three isolates were identified, one of which (pICI 1187) was used in the fermentations described above. FIG. 10 outlines the construction of pICI 1187.

We claim:

1. A process for preparing a polypeptide which comprises ricin A or a structural analogue thereof, which process comprises cultivating a host cell that expresses said polypeptide in a growth medium under either of the following conditions:

(a) cultivating said host cell for an initial period at a first pH value which favours growth of the host cell so that said polypeptide is produced and lowering the pH to a second value and cultivating said host cell for a further period at said second pH value; or (b) maintaining the pH at a value which favours growth of the host cell, and reducing the temperature of the growth medium during the terminal portion of the cultivation;

such that said polypeptide is obtained in soluble form from in the cytoplasmic fraction of the host cell.

2. A process as claimed in claim 1 wherein the process is a fermentation of the fed-batch type and wherein the pH is adjusted before fed-batch conditions are attained.

3. A process as claimed in claim 1 or 2 wherein the temperature is decreased during the terminal portion of the cultivation.

4. A process as claimed in claim 3 wherein the temperature is decreased from about 37° C. to below about 25° C.

5. A process as claimed in claim 1 wherein the host cell is *E. coli* and the polypeptide comprises ricin A.

6. A process as claimed in claim 5 wherein the host cell is *E. coli* DS410.

7. A process as claimed in claim 5 or 6, wherein the pH is lowered from about 6.7 to a value between 6.7 to about 5.5.

8. The method according to claim 1 wherein, when said process comprises step (a), the temperature of said growth medium is reduced during the terminal portion of the cultivation.

9. A process of preparing soluble ricin A which comprises cultivating *E. coli* DS410 transformed with an expression vector containing a ricin A gene and allowing ricin A to accumulate in the cytoplasmic fraction.

10. A process for preparing a polypeptide comprising ricin A or a structural analogue thereof, which process comprises cultivating a host cell capable of expressing said polypeptide in a growth medium at a temperature which favours growth of the host cell and generation of said polypeptide in soluble form in the cytoplasmic fraction of the host cell, cooling the growth medium during the terminal portion of the cultivation, and harvesting the host cell during said terminal portion.

11. A process as claimed in claim 10 wherein the polypeptide comprises ricin A.

12. A process for preparing soluble ricin A or a structural analogue thereof, said process comprising cultivating a host cell transformed with an expression vector containing, under control of a trp promoter, a gene encoding ricin A or a structural analogue thereof, in a growth medium to which is added a supplement containing yeast extract during cultivation and obtaining the expressed soluble protein from the cytoplasmic fraction of the host cell.

13. A process for preparing soluble ricin A which comprises a fermentation of the fed-batch type in which an *E. coli* which is capable of expressing ricin A is cultivated in a growth medium at about pH 6.7, the pH is reduced to a value greater than or equal to about 5.5 and cultivated for a further period, optionally reducing the temperature of the growth medium during the terminal portion of the cultivation and harvesting the soluble ricin A from the cytoplasmic fraction of the host cell during said terminal portion.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

GATAACAACA TATTCCCCAA A 21

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

GATAACAACA TGGTACCCAA A 21

-continued ( 2 ) INFORMATION FOR SEQ ID NO:3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

AACAACATGG TACCCAAACA A 21

( 2 ) INFORMATION FOR SEQ ID NO:4:

( i ) SEQUENCE CHARACTERISTICS:
( A ) LENGTH: 86 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

AAAAAGGGTA TCGACATGGT ACCCGGGGAT CCACCTCAGG GTGGTCTTTC ACATTAGAGG 60

ATAACAACAT GGTACCCAAA CAATAC 86

( 2 ) INFORMATION FOR SEQ ID NO:5:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

AACTAGTACG CAAGTTCACG TAAAAAGGGT ATCGACAATG GTAC 44

( 2 ) INFORMATION FOR SEQ ID NO:6:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

CCATTGTCGA TACCCTTTTT ACGTGAACTT GCGTACTAGT T 41

( 2 ) INFORMATION FOR SEQ ID NO:7:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

GCTTAGCCCG CCTAATGAGC GGGCTTTTTA TCGAT 35

( 2 ) INFORMATION FOR SEQ ID NO:8:

( i ) SEQUENCE CHARACTERISTICS:

-continued ( A ) LENGTH: 32 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

ATCGATAAAA AGCCCGCTCA TTAGGCGGGC TA 32

( 2 ) INFORMATION FOR SEQ ID NO:9:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

AATTCGCATG CGGATCCATC GATC 24

( 2 ) INFORMATION FOR SEQ ID NO:10:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

CCGAGATCGA TGGATCCGCA TGCG 24

( 2 ) INFORMATION FOR SEQ ID NO:11:

( i ) SEQUENCE CHARACTERISTICS:
( A ) LENGTH: 64 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

TCGACATTAT ATTACTAATT AATTGGGGAC CCTAGAGGTC CCCTTTTTTA TTTTAAAAAG 60

CATG 64

( 2 ) INFORMATION FOR SEQ ID NO:12:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

CTTTTTAAAA TAAAAAAGGG GACCTCTAGG GTCCCCAATT AATTAGTAAT ATAATG 56

( 2 ) INFORMATION FOR SEQ ID NO:13:

( i ) SEQUENCE CHARACTERISTICS:
( A ) LENGTH: 8 base pairs
( B ) TYPE: nucleic acid
( C ) STRANDEDNESS: single ( D ) TOPOLOGY: linear ( i i ) MOLECULE TYPE: cDNA ( x i ) SEQUENCE DESCRIPTION: SEQ ID NO:13:

CGGATCCC                                                                                                              8

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CAAGGGGATC CGCATG                                                                                                    16

( 2 ) INFORMATION FOR SEQ ID NO:15:

( i ) SEQUENCE CHARACTERISTICS:
        ( A ) LENGTH: 1140 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 143..943

( x i ) SEQUENCE DESCRIPTION: SEQ ID NO:15:

```
TTCTGGCAAA TATTCTGAAA TGAGCTGTTG ACAATTAATC ATCGAACTAG TTAACTAGTA         60

CGCAAGTTCA CGTAAAAAGG GTATCGACAA TGGTACCCGG GGATCCACCT CAGGGTGGTC        120

TTTCACATTA GAGGATAACA AC ATG GTA CCC AAA CAA TAC CCA ATT ATA AAC        172
                        Met Val Pro Lys Gln Tyr Pro Ile Ile Asn
                         1               5                  10

TTT ACC ACA GCG GGT GCC ACT GTG CAA AGC TAC ACA AAC TTT ATC AGA        220
Phe Thr Thr Ala Gly Ala Thr Val Gln Ser Tyr Thr Asn Phe Ile Arg
                 15                  20                  25

GCT GTT CGC GGT CGT TTA ACA ACT GGA GCT GAT GTG AGA CAT GAA ATA        268
Ala Val Arg Gly Arg Leu Thr Thr Gly Ala Asp Val Arg His Glu Ile
             30                  35                  40

CCA GTG TTG CCA AAC AGA GTT GGT TTG CCT ATA AAC CAA CGG TTT ATT        316
Pro Val Leu Pro Asn Arg Val Gly Leu Pro Ile Asn Gln Arg Phe Ile
         45                  50                  55

TTA GTT GAA CTC TCA AAT CAT GCA GAG CTT TCT GTT ACA TTA GCC CTG        364
Leu Val Glu Leu Ser Asn His Ala Glu Leu Ser Val Thr Leu Ala Leu
     60                  65                  70

GAT GTC ACC AAT GCA TAT GTG GTC GGC TAC CGT GCT GGA AAT AGC GCA        412
Asp Val Thr Asn Ala Tyr Val Val Gly Tyr Arg Ala Gly Asn Ser Ala
75                  80                  85                  90

TAT TTC TTT CAT CCT GAC AAT CAG GAA GAT GCA GAA GCA ATC ACT CAT        460
Tyr Phe Phe His Pro Asp Asn Gln Glu Asp Ala Glu Ala Ile Thr His
                 95                 100                 105

CTT TTC ACT GAT GTT CAA AAT CGA TAT ACA TTC GCC TTT GGT GGT AAT        508
Leu Phe Thr Asp Val Gln Asn Arg Tyr Thr Phe Ala Phe Gly Gly Asn
            110                 115                 120

TAT GAT AGA CTT GAA CAA CTT GCT GGT AAT CTG AGA GAA AAT ATC GAG        556
Tyr Asp Arg Leu Glu Gln Leu Ala Gly Asn Leu Arg Glu Asn Ile Glu
        125                 130                 135
```

-continued

TTG GGA AAT GGT CCA CTA GAG GAG GCT ATC TCA GCG CTT TAT TAT TAC 604
Leu Gly Asn Gly Pro Leu Glu Glu Ala Ile Ser Ala Leu Tyr Tyr Tyr
140 145 150

AGT ACT GGT GGC ACT CAG CTT CCA ACT CTG GCT CGT TCC TTT ATA ATT 652
Ser Thr Gly Gly Thr Gln Leu Pro Thr Leu Ala Arg Ser Phe Ile Ile
155 160 165 170

TGC ATC CAA ATG ATT TCA GAA GCA GCA AGA TTC CAA TAT ATT GAG GGA 700
Cys Ile Gln Met Ile Ser Glu Ala Ala Arg Phe Gln Tyr Ile Glu Gly
175 180 185

GAA ATG CGC ACG AGA ATT AGG TAC AAC CGG AGA TCT GCA CCA GAT CCT 748
Glu Met Arg Thr Arg Ile Arg Tyr Asn Arg Arg Ser Ala Pro Asp Pro
190 195 200

AGC GTA ATT ACA CTT GAG AAT AGT TGG GGG AGA CTT TCC ACT GCA ATT 796
Ser Val Ile Thr Leu Glu Asn Ser Trp Gly Arg Leu Ser Thr Ala Ile
205 210 215

CAA GAG TCT AAC CAA GGA GCC TTT GCT AGT CCA ATT CAA CTG CAA AGA 844
Gln Glu Ser Asn Gln Gly Ala Phe Ala Ser Pro Ile Gln Leu Gln Arg
220 225 230

CGT AAT GGT TCC AAA TTC AGT GTG TAC GAT GTG AGT ATA TTA ATC CCT 892
Arg Asn Gly Ser Lys Phe Ser Val Tyr Asp Val Ser Ile Leu Ile Pro
235 240 245 250

ATC ATA GCT CTC ATG GTG TAT AGA TGC GCA CCT CCA CCA TCG TCA CAG 940
Ile Ile Ala Leu Met Val Tyr Arg Cys Ala Pro Pro Pro Ser Ser Gln
255 260 265

TTT TGATTGCTTA TAAGGCCAGT GGTACCCGGG GATCCTCTAG AGTCGACCTG 993
Phe

CAGGCATGCA AGCTTAGCCC GCCTAATGAG CGGGCTTTTT TTTATCGACC GATGCCCTTG 1053

AGAGCCTTCA ACCCAGTCAG CTCCTTCCGG TGGGCGCGGG GCATGACTAT CGTCGCCGCA 1113

CTTATGACTG TCTTCTTTAT CATGCAA 1140

( 2 ) INFORMATION FOR SEQ ID NO:16:

( i ) SEQUENCE CHARACTERISTICS:
( A ) LENGTH: 267 amino acids
( B ) TYPE: amino acid
( D ) TOPOLOGY: linear ( i i ) MOLECULE TYPE: protein ( x i ) SEQUENCE DESCRIPTION: SEQ ID NO:16:

Met Val Pro Lys Gln Tyr Pro Ile Ile Asn Phe Thr Thr Ala Gly Ala
1 5 10 15

Thr Val Gln Ser Tyr Thr Asn Phe Ile Arg Ala Val Arg Gly Arg Leu
20 25 30

Thr Thr Gly Ala Asp Val Arg His Glu Ile Pro Val Leu Pro Asn Arg
35 40 45

Val Gly Leu Pro Ile Asn Gln Arg Phe Ile Leu Val Glu Leu Ser Asn
50 55 60

His Ala Glu Leu Ser Val Thr Leu Ala Leu Asp Val Thr Asn Ala Tyr
65 70 75 80

Val Val Gly Tyr Arg Ala Gly Asn Ser Ala Tyr Phe Phe His Pro Asp
85 90 95

Asn Gln Glu Asp Ala Glu Ala Ile Thr His Leu Phe Thr Asp Val Gln
100 105 110

Asn Arg Tyr Thr Phe Ala Phe Gly Gly Asn Tyr Asp Arg Leu Glu Gln
115 120 125

Leu Ala Gly Asn Leu Arg Glu Asn Ile Glu Leu Gly Asn Gly Pro Leu
130 135 140

-continued

Glu Glu Ala Ile Ser Ala Leu Tyr Tyr Tyr Ser Thr Gly Gly Thr Gln
145 150 155 160

Leu Pro Thr Leu Ala Arg Ser Phe Ile Ile Cys Ile Gln Met Ile Ser
165 170 175

Glu Ala Ala Arg Phe Gln Tyr Ile Glu Gly Glu Met Arg Thr Arg Ile
180 185 190

Arg Tyr Asn Arg Arg Ser Ala Pro Asp Pro Ser Val Ile Thr Leu Glu
195 200 205

Asn Ser Trp Gly Arg Leu Ser Thr Ala Ile Gln Glu Ser Asn Gln Gly
210 215 220

Ala Phe Ala Ser Pro Ile Gln Leu Gln Arg Arg Asn Gly Ser Lys Phe
225 230 235 240

Ser Val Tyr Asp Val Ser Ile Leu Ile Pro Ile Ile Ala Leu Met Val
245 250 255

Tyr Arg Cys Ala Pro Pro Pro Ser Ser Gln Phe
260 265

( 2 ) INFORMATION FOR SEQ ID NO:17:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..18

( x i ) SEQUENCE DESCRIPTION: SEQ ID NO:17:

TCA CAG TTT TCT TTG CTT 18
Ser Gln Phe Ser Leu Leu
1 5

( 2 ) INFORMATION FOR SEQ ID NO:18:

( i ) SEQUENCE CHARACTERISTICS:
( A ) LENGTH: 6 amino acids
( B ) TYPE: amino acid
( D ) TOPOLOGY: linear ( i i ) MOLECULE TYPE: protein ( x i ) SEQUENCE DESCRIPTION: SEQ ID NO:18:

Ser Gln Phe Ser Leu Leu
1 5

( 2 ) INFORMATION FOR SEQ ID NO:19:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..9

( x i ) SEQUENCE DESCRIPTION: SEQ ID NO:19:

TCA CAG TTT TGATTGCTT 18
Ser Gln Phe
1

-continued ( 2 ) INFORMATION FOR SEQ ID NO:20:

( i ) SEQUENCE CHARACTERISTICS:
( A ) LENGTH: 3 amino acids
( B ) TYPE: amino acid
( D ) TOPOLOGY: linear ( i i ) MOLECULE TYPE: protein ( x i ) SEQUENCE DESCRIPTION: SEQ ID NO:20:

```
Ser Gln Phe
  1
```

( 2 ) INFORMATION FOR SEQ ID NO:21:

( i ) SEQUENCE CHARACTERISTICS:
( A ) LENGTH: 172 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:21:

```
AATTCTGGCA AATATTCTGA AATGAGCTGT TGACAATTAA TCATCGAACT AGTTAACTAG    60
TACGCAAGTT CACGTAAAAA GGGTATCGAC AATGGTACCC GGGGATCCTC TAGAGTCGAC   120
CTGCAGGCAT GCAAGCTTAG CCCGCCTAAT GAGCGGGCTT TTTTTTATCG AC           172
```

( 2 ) INFORMATION FOR SEQ ID NO:22:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:22:

```
TCGACATTAT ATTACTAATT AATTGGGGAC CCTAGAGGTC CCCTTTTTTA TTTTAAAAAG    60
CATGCGGATC CC                                                        72
```

( 2 ) INFORMATION FOR SEQ ID NO:23:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:23:

```
CAAGGGGATC CGCATGCTTT TTAAAATAAA AAAGGGGACC TCTAGGGTCC CCAATTAATT    60
AGTAATATAA TG                                                        72
```